(12) United States Patent
Chornenky et al.

(10) Patent No.: US 9,486,638 B2
(45) Date of Patent: Nov. 8, 2016

(54) THERMALLY ASSISTED PULSED ELECTRO-MAGNETIC FIELD STIMULATION DEVICE AND METHOD FOR TREATMENT OF OSTEOARTHRITIS

(71) Applicant: Minnesota Medical Physics LLC, Edina, MN (US)

(72) Inventors: Victor I. Chornenky, Minnetonka, MN (US); Ali Jaafar, Eden Prairie, MN (US)

(73) Assignee: Minnesota Medical Physics LLC, Edina, MN (US)

( * ) Notice: Subject to any disclaimer, the term of this patent is extended or adjusted under 35 U.S.C. 154(b) by 0 days.

(21) Appl. No.: 14/594,897

(22) Filed: Jan. 12, 2015

(65) Prior Publication Data

US 2015/0217125 A1 Aug. 6, 2015

Related U.S. Application Data

(63) Continuation of application No. 13/934,875, filed on Jul. 3, 2013, now Pat. No. 8,932,196, which is a continuation-in-part of application No. 13/421,807, filed on Mar. 15, 2012, now Pat. No. 8,827,886, which is a continuation-in-part of application No. 12/878,028, filed on Sep. 8, 2010, now Pat. No. 8,460,167, and a continuation of application No. PCT/US2011/050858, filed on Sep. 8, 2011.

(60) Provisional application No. 61/467,968, filed on Mar. 25, 2011, provisional application No. 61/276,512, filed on Sep. 14, 2009.

(51) Int. Cl.

| *A61N 2/00* | (2006.01) |
|---|---|
| *A61F 7/02* | (2006.01) |
| *A61N 2/02* | (2006.01) |
| *A61N 1/40* | (2006.01) |
| *A61F 7/00* | (2006.01) |

(52) U.S. Cl.
CPC ............... *A61N 2/002* (2013.01); *A61F 7/02* (2013.01); *A61N 1/40* (2013.01); *A61N 2/004* (2013.01); *A61N 2/006* (2013.01); *A61N 2/02* (2013.01); *A61F 2007/009* (2013.01); *A61F 2007/0024* (2013.01); *A61F 2007/0086* (2013.01); *A61F 2007/0093* (2013.01); *A61F 2007/0096* (2013.01); *A61F 2007/0228* (2013.01)

(58) Field of Classification Search
CPC .......... A61N 1/40; A61N 2/004; A61N 2/02; A61N 2/002; A61F 2007/0024; A61F 7/02; A61F 2007/0086; A61F 2007/0228; A61F 2007/0096; A61F 2007/0093; A61F 2/006; A61F 2007/009
See application file for complete search history.

(56) References Cited

U.S. PATENT DOCUMENTS

| 5,181,902 A * | 1/1993 | Erickson | A61N 2/02 600/13 |
|---|---|---|---|
| 6,418,345 B1 * | 7/2002 | Tepper | A61N 2/02 600/14 |
| 7,207,953 B1 * | 4/2007 | Goicaj | A61H 23/02 601/134 |

(Continued)

*Primary Examiner* — Christine H Matthews
*Assistant Examiner* — Joshua D Lannu
(74) *Attorney, Agent, or Firm* — Skaar Ulbrich Macari, P.A.

(57) ABSTRACT

A method, apparatus and a system for thermally-assisted pulsed electromagnetic field stimulation for treatment of osteoarthritis are disclosed. In one embodiment, the system comprises a multi-coil applicator adapted for positioning near or around of the treated joint, a pulse generator functionally coupled to the applicator, a power supply, and a feedback loop for stabilizing the temperature of the joint. The feedback loop includes a heating element, a temperature sensor and an electronic controller for maintaining the temperature of the joint in the range of 38 to 42 degree C. At elevated temperatures the healing effect of PEMF stimulation on the cartilage is maximized and overall efficiency of the treatment is improved. To produce a high electric field, the coils of the applicator are made with a low number of turns, for example less than 5 turns, and are spatially arranged to cover the whole joint without "dead" zones.

14 Claims, 28 Drawing Sheets

(56) References Cited

U.S. PATENT DOCUMENTS

| | | | |
|---|---|---|---|
| 2005/0228462 A1* | 10/2005 | Brighton | A61N 2/02 607/51 |
| 2008/0125618 A1* | 5/2008 | Anderson | A61N 2/02 600/14 |
| 2008/0288035 A1* | 11/2008 | Gill | A61F 7/007 607/108 |

* cited by examiner

THERMALLY ASSISTED PULSED ELECTRO-MAGNETIC FIELD STIMULATION DEVICE AND METHOD FOR TREATMENT OF OSTEOARTHRITIS

PRIORITY

This application is a continuation of U.S. patent application Ser. No. 13/934,875, filed Jul. 3, 2013, which is a continuation-in-part of U.S. patent application Ser. No. 13/421,807, filed Mar. 15, 2012, now U.S. Pat. No. 8,827,886, which is a continuation of international application PCT/US2011/050858, filed Sep. 8, 2011, and also claims benefit of U.S. Provisional Patent Application Ser. No. 61/467,968, filed Mar. 25, 2011. U.S. patent application Ser. No. 13/421,807 is a continuation-in-part of U.S. patent application Ser. No. 12/878,028, filed on Sep. 8, 2010, now U.S. Pat. No. 8,460,167, which claims priority benefit of U.S. Provisional Patent Application Ser. No. 61/276,512, filed Sep. 14, 2009. All of the above-mentioned applications and patents are hereby incorporated herein by reference in their entirety.

FIELD

The invention relates to a method and apparatus for pain management, anti-inflammation and treatment of osteoarthritis. More particularly, the invention relates to an apparatus for producing pulsed electromagnetic field in arthritic joints, and a method for treating osteoarthritis utilizing pulsed electromagnetic fields.

BACKGROUND

Osteoarthritis (OA), sometimes called degenerative joint disease, is a chronic disorder associated with damage to the articular cartilage and surrounding tissues and characterized by pain, stiffness and loss of function. OA commonly affects the hands, spine, and large weight-bearing joints, such as the hips and knees. OA affects nearly 21 million people in the United States, accounting for 25% of visits to primary care physicians. 80% of US population have radiographic evidence of OA by age 65, and 60% of those are symptomatic. In the United States, hospitalizations for osteoarthritis soared from 322,000 in 1993 to 735,000 in 2006.

Articular cartilage is the smooth white tissue that covers the surface of all the synovial joints in the human body. Its main function is to facilitate the movement of one bone against another. With the coefficient of friction as low as 0.003 and the ability to bear compressive loads as high as 20 MPa, articular cartilage is ideally suited for placement in joints, such as the knee and hip. Articular cartilage is composed mainly of water (70-80% by wet weight). It contains specialized cells called chondrocytes that produce a large amount of extracellular matrix composed of collagen, chondroitin and keratan sulfate proteoglycan. Collagen forms a network of fibrils, which resists the swelling pressure generated by the proteoglycans, thus creating a swollen, hydrated tissue that resists compression. Cartilage is one of the few tissues in the body that does not have its own blood supply. For nutrition and release of waste products chondrocytes depend on diffusion helped by the pumping action generated by compression of the cartilage. Compared to other connective tissues, cartilage grows and repairs more slowly.

In addition to proteins and proteoglycans that comprise the extracellular matrix, the chondrocytes produce the enzymes causing degradation of the matrix. This way the chondrocytes maintain a permanent turnover and rejuvenation of the cartilage.

The chondrocytes and the cartilage matrix change with advancing age. The chondrocytes are responsible for both the production of new matrix proteins and the enzymes related to the cartilage degradation. It is generally accepted that the osteoarthritis process includes alterations in the normal balance between synthesis and degradation of articular cartilage and the subchondral bone. In younger individuals the chondrocytes are capable of the appropriate maintenance of the cartilage tissue and keeping it healthy and functional. But with advancing age, the chondrocytes become incapable of providing adequate repair and the process is tipped towards degeneration.

For many years healthy cartilage tissue not only preserves its integrity and function but also performs a constant remodeling to meet requirements of changing loads on the joints. Multiple regulatory pathways by which chondrocytes in articular cartilage sense and respond to the mechanical stimuli have been discovered in recent studies. One of the pathways is a mechanical one, in which the chondrocytes sense the pressure on the cartilage and respond by gene transcription, translation and post-translational modification of the extracellular matrix. Another pathway is a cellular response to the electrical signals generated by the loaded cartilage tissue. It was discovered that an electric potential appears on a cartilage tissue if it is mechanically stressed. It was shown also, that the electric signal on a loaded cartilage tissue can be produced by two physical phenomena: a piezoelectric effect and a streaming potential.

Piezoelectric effect is the ability of some materials to generate an electric field in response to applied mechanical stress. Piezoelectric effect has been observed in a number of soft and hard tissues (including cartilage and bone) and appears to be associated with the presence of oriented fibrous proteins such as collagen. A deformation of a protein molecule produces asymmetric shift of the opposite electric charges comprising the molecule and results in a macroscopic electric potential on the stressed tissue.

A streaming potential is produced when a liquid is forced to flow through a capillary or porous solids (including cartilage and bone). The streaming potential results from the presence of an electrical double layer at the solid-liquid interface. This electrical double layer is made up of ions of one charge type which are fixed to the surface of the solid and an equal number of mobile ions of the opposite charge which are distributed through the neighboring region of the liquid phase. A mechanical stress applied to such a system creates a flow of the mobile ions with respect to the fixed ions on the solid which constitutes an electric current. The electric potential on the tissue generated by this current is called a streaming potential.

Whatever the relative contribution of these two mechanisms is in the electric signal on the stressed tissue, a substantial electric potential is created across the loaded cartilage. It has been suggested that this stress-generated potential (SGP) may play a significant role in cartilage growth, repair, and remodeling. Moreover, because SGP provides a link between physiology and physics it may open a new opportunity of influencing biological processes in the articular cartilage. It has been proven by numerous studies that increase in chondrocytes cell division and the collagen and proteoglycan synthesis are possible and may be achieved in vivo by applying electric potential to the cartilage. This can be done with relatively simple medical devices. In the future these devices promise to become a new non-invasive modality of treatment of arthritis and other cartilage diseases.

Currently available treatment options for osteoarthritis focus on symptoms relief, whereas truly disease-modifying agents are lacking. Thus, the basic therapy includes common analgesics, non-steroidal anti-inflammatory drugs (NSAID), physical therapy and eventually, in severe cases, joint replacement surgery. Conventionally, physicians treat patients exhibiting symptomatic osteoarthritis by the administration of a NSAID. Many such non-steroidal anti-inflammatory drugs are known and are often effective in reducing the symptoms of osteoarthritis. NSAIDs have demonstrated ability to relieve pain, improve activity level, and in some cases improve function of the arthritic joints. None of these drugs, however, have been proven in carefully controlled clinical trials to reverse the long term natural history of osteoarthritis. Moreover, while many of these drugs have demonstrated effectiveness in treating the symptoms of osteoarthritis, they also have been associated with significant toxicities and other risks, such as deleterious effects on cartilage when used over prolonged periods of time. Moreover, in addition to NSAID being very expensive, the toxicities of these drugs limit their usefulness, particularly in elderly patients. Side effects from NSAIDs could be severe; they cause over 20,000 deaths annually in US.

Appropriate exercises, including stretching, strengthening, and postural exercises help maintain healthy cartilage, increase joint's range of motion and strengthen surrounding muscles so that they can absorb stress better. Exercises can sometimes stop or even reverse osteoarthritis of the hips and knees.

Heat Therapy: Heat increases blood flow and makes connective tissue more flexible. It temporarily blocks pain, helps reduce inflammation, stiffness, and improves range of motion. Heat may be applied to the body surface or to deep tissues. Hot packs, infrared heat and hydrotherapy provide surface heat. Electric currents or ultrasound generate heat in deep tissues. Research shows that heat disrupts the body's usual pain cycle by stimulating heat sensors and preventing sensation of pain from reaching the brain. Because the cartilage tissue does not have its own pain receptors, sensation of pain in affected joints comes from underlying bones which are rich in pain receptors. Namely these receptors are blocked by the heat. As of today, there is no direct evidence that the heat therapy itself can reverse or even slow down degeneration of the cartilage affected by arthritis.

Pulsed Electromagnetic Field (PEMF) therapy is known for several decades. It started from observations made by several researchers in seventies decade of the last century that the pulsed magnetic field had a positive effect on healing bone fractures and damaged cartilages. At that time many researches believed that the healing effect was produced by the magnetic field itself and many PEMF applicators with different temporal and spatial patterns of applied magnetic field were claimed as beneficial and patented. The differences between the patented features in the designs of the applicators and methods of treatment were in the amplitudes, lengths of magnetic pulses, their shapes, mainly rectangular and sinusoidal, repetition rates (frequencies), geometry and electrical parameters of the coils. Also, a lot of efforts and creativity were directed to the ergonomics of the PEMF applicators and methods of their positioning near or securing to the human body. It was perceived then that the most important therapeutic parameter of the system was the amplitude of the magnetic field, so the coils were built with high numbers of turns and the pulsed magnetic fields up to hundreds of Gauss were generated.

Alternating electrical fields for the same purpose of bone fracture healing and treatment of damaged cartilages were exploited by several research groups in laboratory studies and clinical trials. Even though the electrical field applicators in these studies proved to be therapeutically effective they revealed a serious drawback—necessity to implant electrodes into the vicinity of the treatment area or at least apply electrodes from outside the body with electrically intimate contact to the skin. In comparison with the electrical systems the PEMF applicators have advantage of not only being non invasive, but also not requiring an intimate electrical contact with the skin. Contrary to the electric field, magnetic field at the employed frequencies easily penetrates the human body practically to any depth.

In an electric field stimulation system developed by Brighton et all (U.S. Pat. No. 7,158,835 B2 and others of the same inventor) a sinusoidal frequency of 60 kHz was employed. This relatively high frequency allowed achieving good capacitance coupling of the treatment volume of the joint with the electrodes at the skin adjacent to the joint. Clinical success of the 60 kHz system proved that the stimulating effect on the cartilage can be achieved with much higher frequencies then tens or hundreds of Hz. It can be expected that the therapeutic effect of the electric fields on cartilage and bone healing exists in a frequency range from a fraction of Hz to up to at least 60 kHz.

Now it is common knowledge among researchers that the active agent of the PEMF systems is the electric field. Namely electric field interacts with biological tissues, not the magnetic field. From general theory of electromagnetic field it is known that an electric field accompanies every change in time of the magnetic field. Being more specific, the electric field E, created by varying magnetic field, is directly proportional to the time derivative of the magnetic inductance B. The energy associated with the electric field also comes from the magnetic field. It should be noted that the electric field created by a changing magnetic field has one significant difference from the electric field created by electric charges at rest (electrostatic fields): it is a curly field, not potential as the field produced by the electric charges. Contrary to the potential field, in which the field lines begin on positive charges and terminate on the negative charges, the field lines of the curl electric field are continuous; they form close loops, very much as the magnetic field lines around a wire with an electric current. This nature of the curly electric field imposes some limitations on the way the devices, whose intended use is the application of the electric field to human body, should be built. One of these limitations is the presence of areas with very low electric fields, "dead zones". The dead zones are located near the axes of the electromagnetic coils and produce no therapeutic effect on the treated tissue. In details they will be discussed further herein.

In U.S. Pat. No. 5,842,966 issued to Markoll a method for treatment of arthritis is disclosed. The method involves treating organs by applying a magnetic field by means of an annular coil surrounding the organ, the coil being energized by a pure DC voltage having a rectangular wave form pulsing at the rate of 1-30 CPS. The invention also includes an apparatus comprising a body support encompassed by an annular coil energized as above. The coil is mounted on a carriage running on tracks adjacent the body support. This disclosed device and method has a dead zone along the center axis of the coil.

In U.S. Pat. No. 7,158,835 B2 issued to Brighton et al, a PEMF device is disclosed for preventing and treating osteoporosis, hip and spine fractures, or spine fusions by incorporating a conductive coil into a garment adapted to be worn adjacent to a treatment area and applying an electrical signal to the coil to produce a magnetic flux that penetrates the treatment area and produces an electric field in the bones and the treatment area. The disclosed device has dead zones along the center axes of the coils. The device does not include any heating means.

In U.S. Pat. No. 6,701,185 issued to Burnett et al, an apparatus for electromagnetic stimulation of nerve, muscle, and body tissues is disclosed. The apparatus is comprised of a plurality of overlapping coils which are able to be independently energized in a predetermined sequence such that each coil will generate its own independent electromagnetic field and significantly increase the adjacent field. The coils are co-planar and are disposed in an ergonomic body wrap, which is properly marked to permit an unskilled patient to locate the body wrap, on a particular part of the body, of the patient so that the stimulation coils will maximize the electromagnetic stimulation on the selected nerves, muscles, and/or body tissues near the treated area. The device can be used to treat medical conditions including: muscular atrophy, neuropathic bladder and bowel, musculoskeletal pain, arthritis, as well as possible future applications in the prevention of deep vein thrombosis and weight reduction. This PEMF device has much more uniform electrical field than a simple coil and does not have dead zones. The device does not have a heating element and does not provide PEMF treatment at elevated temperatures.

In U.S. Pat. No. 6,179,772 issued to Blackwell a portable electronic PEMF apparatus is disclosed. The apparatus comprises a PEMF coil, power supply, and electronic switching means. The power supply along with the switching means provide periodic electric power to the PEMF coil. The PEMF coil comprises multiple turns of a conductive wire around a core. The core comprises a magnetic shield layer of materials such as mu metal or soft iron. The power supply comprises a battery, a regulated voltage source and unregulated voltage source from the battery and electronic switching circuit. The electronic switching circuit is tuned to periodically provide power to the coil at a frequency to generate a non-inverting, varying electromagnetic field from the coil. Disclosed apparatus also comprises a heating means. This heating means that provides heat to a body part under treatment is an electric resistive heater, or, in another implementation, a chemical heater. In both cased the applied heat is not regulated and the temperature of the treatment area is not controlled.

In a patent application US 20080288035 filed by Jagjit et al, a stimulation device for treating osteoarthritis is disclosed. The device is intended for therapeutic treatment to a body part such as a joint to promote healing of the body part. It comprises a signal generator for generating a pulsed electromagnetic field based upon a selected treatment mode, a controller for storing the treatment mode and communicating the treatment mode to the signal generator, a heat source configured to provide thermal therapy to the body part, and monitoring means for monitoring the electromagnetic field generated by the electromagnetic stimulating means. Disclosed device uses a heat or cold source to block pain. The cold and heat sources, mainly chemical in nature, are not controlled by any means; they have drifting temperatures and do not provide PEMF therapy in the optimal range of temperatures for osteoarthritis treatment.

As noted in the above discussion, drawbacks of the existing PEMF systems include: not efficient production of the electric field; not uniform coverage of the treatment zone with the electric field, presence of dead zones. As it will be discussed further herein, from the stand point of arthritis treatment, the PEMF systems that provide therapy at ambient temperatures or use uncontrolled heating and/or cooling of the joint do not take advantage of providing treatment at the optimal range of temperatures for the cartilage treatment. Therefore, there is a need for an improved device and method for treating OA that remedy the drawbacks of the prior art treatment devices and methods.

SUMMARY

The present invention effectively addresses certain drawbacks in the prior art OA treatment devices and methods. One object of certain embodiments of the present invention is to increase the amplitude of pulsed electric field generated by PEMF systems. Another object of certain embodiments of the invention is to improve efficiency of PEMF therapy for arthritis by providing more uniform spatial distribution of the pulsed electric fields and eliminating dead zones in the treatment volume. Yet another object of certain embodiments of the present invention is to improve efficiency of the PEMF treatment of arthritis by providing treatment at optimal temperatures of the joints, at which chondrocytes in the cartilage tissue have maximum metabolism and vitality.

A further object of certain embodiments is to make simple and ergonomically sound Thermally Assisted PEMF treatment systems for various body parts, including the neck, knee, back, hand and wrist with easy to use applicators. Another object of certain embodiments is to simplify production of the PEMF applicator and reduce the number of different sizes of the applicators needed to be maintained for a broad variety of patient sizes. Yet another object of certain embodiments is to provide improved heat transfer from the coils of the applicators to the treatment area.

In accordance with one aspect of certain embodiments of the invention, electromagnetic coils producing pulsed electromagnetic field in the arthritic joints are made of a low number of turns, preferably in the range of 1 to 10 turns, more preferably in the range of 1 to 6 turns, or even less than one full turn. In this range of numbers of turns the inductance L of the coils varies from a fraction of one micro Henry to several micro Henry. Assuming that the resistance of coils R is in a milliohms range, the time of relaxation of the coils L/R ranges between 10 and 200 microseconds, which allows for pulse durations range about of 5 to 50 microseconds. With that low inductance and short pulses even for voltages used for powering the coils being as low as 12-24 V, the rate of change of the electric current in the coil can be extremely high, up to tens of millions Amperes per second. As a result, an electric field E induced around the coil by the rapidly changing magnetic field will achieve tens to hundreds of mV/cm. This way of generating of electric field is much more efficient than that with high numbers of turns and higher inductances of the coils. The magnitude of the electric field about E=100 mV/cm is a typical value of the endogenous electric fields generated by the body tissues during wound healing or during development or regeneration of tissues in the body. Electric field E=100 mV/cm is a safe and biologically efficient value of the electric field in the body. This value may be considered as a standard to be matched or at least to be approached by exogenous electric fields provided by the PEMF therapy.

The PEMF coils that have only several turns and are made of multi-strand thin wires are compatible in texture with elastic fabrics and may be used for ergonomic applicators for different parts of human body.

A coil made of less than one full turn of a wire is topologically different from the coils made of several full turns. It represents an open loop. As any open loop it can be wrapped around a joint instead of being pulled over it. This feature presents an additional advantage of enabling construction of an ergonomic PEMF applicator in which the coil can be physically placed around a joint by simple wrapping around it without being stretched and pulled over it. This PEMF applicator can be built, for example for knee, as non elastic wrap and still be an applicator type "one size fits all".

In accordance with another aspect of certain embodiments of the invention, the PEMF applicators are configured in such a manner that they don't have "dead zones", or arias in which the electric field induced by the PEMF coils is too low to cause any therapeutic effect in the cartilage. In one particular embodiment, a plurality of coils (at least two) comprising this applicator are placed at different positions around or near the joint to cover all parts of the joint with an electric field of a sufficient amplitude and right direction. The coils may be powered individually in sequence or in pairs in sequence. The direction of the induced electric field is selected mainly along the body of cartilage, so the electric field can produce significant electric current inside the cartilage tissue. Preferentially, the lines of the electric field should not cross the bones around the joint because in this case the high resistance of the bone will drastically reduce the current along the electric lines and there will be no significant current and, consequently, electric field inside the cartilage tissue. One example of an applicator inducing the electric field in right direction is a back applicator, described below, in which the electric field is induced by two coils circumferentially along the intervertebral disk.

In accordance with yet another aspect of certain embodiments of this invention, PEMF treatment is performed at elevated temperatures of the joint. In one implementation, the joint is heated by the ohmic heat deposited in the coils during a pulse and by the energy stored in the magnetic field of the electromagnetic coils that is converted into heat after the pulse. At the end of a pulse during which a coil is connected to a DC power supply, the DC power supply is disconnected from the coil and the current through the coil is redirected into a closed loop made by the coil and a high current diode, called a "free wheel diode". During this time which is defined by a time of relaxation L/R of this circuit, the current in the closed loop is supported by the magnetic energy of the coil. The magnetic energy stored in the coil is several times higher than the ohmic heat deposited during the pulse. When the current through the closed loop decreases to zero, the whole magnetic energy is also deposited in the coil and the free wheel diode as heat. The free wheel diode can have a forward bias of 0.5-1.0V. When a high current passes through it, a significant amount of power equivalent to the current times the forward bias is converted into heat within the diode.

The PEMF system may include an intermediate heat exchanger which, on one hand, serves as a heat sink for the coil and the "free wheel diode", taking heat from them and, on the other hand, as a heat pads for the joint. The heat exchanger may comprise a dielectric material with high thermal conductivity, such as a ceramic or plastic. A feature of such thermally assisted PEMF is that the temperature of the heating pads is stabilized in the range 39-42 C.°. At these elevated temperatures metabolism of chondrocytes is higher than at normal ambient temperatures, so, the production of molecules of different proteins, proteoglycans, chondroitins and other important components of the extracellular matrix, substantially increases, making PEMF therapy more efficient. It should be mentioned though, that if the temperature of the joint for some significant time is above or equal 43 C.°, production of component of the extracellular matrix sharply decreases, chondrocytes start producing so called heat proteins protecting them from heat damage and PEMF therapy becomes not efficient.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1A:
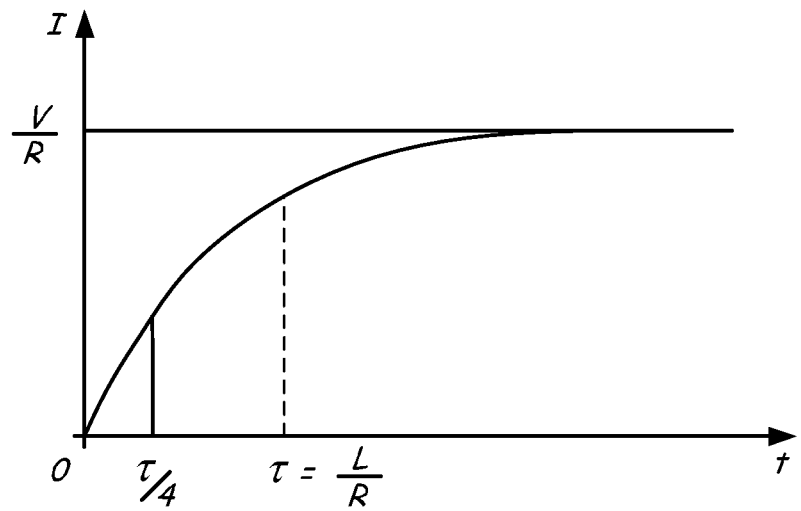
FIG. 1A is a graph of current I(t) of the coil as a function of time according to an example embodiment.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various example embodiments; nevertheless, these example embodiments are not intended to limit the present invention to any specific example, embodiment, environment, application, or particular implementation described herein. Therefore, descriptions of these example embodiments are only provided for purpose of illustration rather than to limit the present invention.

A useful understanding of the properties of the curly electric field generated by an electromagnetic coil can be achieved from an analytical expression for the electric current through the coil as a function of time and analysis of the distribution of the electric field in and around the coil.

For a coil with inductance L and resistance R connected to a DC power supply with voltage U the current through the coil is described by a known function of time:

$$I(t)=U/R(1-\exp(-t/\tau)) \quad (1)$$

Where $\tau=L/R$—is so called a relaxation time of a RL circuit. Simple differentiation of this expression gives the time derivative of the current:

$$dI(t)/dt=-(U/L)\exp(-t/\tau) \quad (2)$$

Figure 1B:
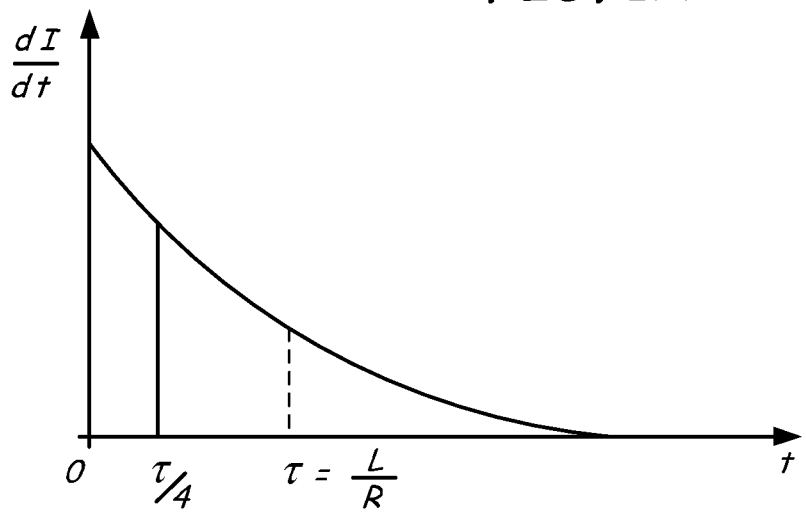
FIG. 1B is a graph of the current time derivative dI(t)/dt as a function of time according to an example embodiment.

FIGS. 1A and 1B, respectively, show graphs of current I(t) and its time derivative dI(t)/dt, both as functions of time. The graphs can be divided roughly in two parts, the right one for $t\gg\tau$, where the current is approaching to its ohmic limit U/R while the time derivative dI(t)/dt is close to zero, and the left part for $t\leq 5\tau$, where the current exponentially increases from zero to almost the ohmic limit U/R and where the time derivative sharply decreases from the maximum value of U/L to a close to zero value. As current through the coil increases, an electric field, which is proportional to the time derivative of the current, is generated around the coil. At the time $t=\tau$ the time derivative of the current and, consequently, the curl electric field generated by the coil is equal to 37% of its maximum value at t=0, at the time $t=0.25\tau$ it is equal to 78%, and at the time $t=0.2\tau$ it is equal to 82% of its maximum value. As can be seen, the generation of the curl electric field is the most efficient when a PEMF coil is activated by pulses not longer than $0.2\tau$ to $0.25\tau$. At the end of the pulse with duration $0.25\tau$ the maximum current Imax through the coil will be $dI(0)/dt\times 25\tau=U/L\times 0.25L/R=0.25U/R$. Therefore, to achieve efficient generation of the electric field the maximum current through the coil at the end of a pulse should be about $$Imax=0.25U/R \quad (3)$$

For safety reasons the operating voltage U should be below 36 Volts. The following discussion will assume that the voltage is 20V. Semiconductor current switches capable of commutating currents up to 200-300 Amps are available on the market. The following discussion assumes a 200 Amp switch. From formula (3) it follows that for a given voltage and maximum current the required resistance should be R=0.25U/Imax=0.025 Ohm. This is the resistance of the coil itself plus resistance of a switch and a wiring between the coil and the DC power source.

The electric field generated by the PEMF coil can be estimated using a simple expression for the magnetic field B generated by a short circular coil at its center.

$$B=\mu_0 NI/D \quad (4)$$

Here, $\mu_0=4\pi 10^{-7}$—magnetic permeability of vacuum, N—number of turns and D is the diameter of the coil. Differentiation of the expression (4) over time gives us:

$$dB/dt=\mu_0 N(dI/dt)/D \quad (5)$$

Substituting expression for the time derivative of the current from expression (2), we will get:

$$dB/dt=\mu_0 N(U/(LD))\exp(-t/\tau) \quad (6)$$

For the induction of a short circular coil we can use an expression from (H. Knoepfel, *Magnetic fields*, John Wiley & sons, New York, 2000):

$$L=0.5\mu_0 N^2 D(\ln(8D/d)-7/4), \quad (7)$$

where d is the diameter of the wire. After substituting (7) into equation (6) we will get for the time derivative of magnetic inductance dB/dt:

$$dB/dt=(U/(ND^2(\ln(8D/d)-7/4)))\exp(-t/\tau) \quad (8)$$

Inferring an expression for the electric field E induced by changing magnetic field B of the coil can be performed using a Faraday law of inductance:

$$\oint Edl=-d/dt\iint BdA \quad (9)$$

Here on the left is the electromotive force, a contour integral taken along a closed loop in the magnetic field. On the right is a time derivative of a surface integral taken over a surface A pulled on the closed loop. This surface integral is called a magnetic flux.

Figure 2:
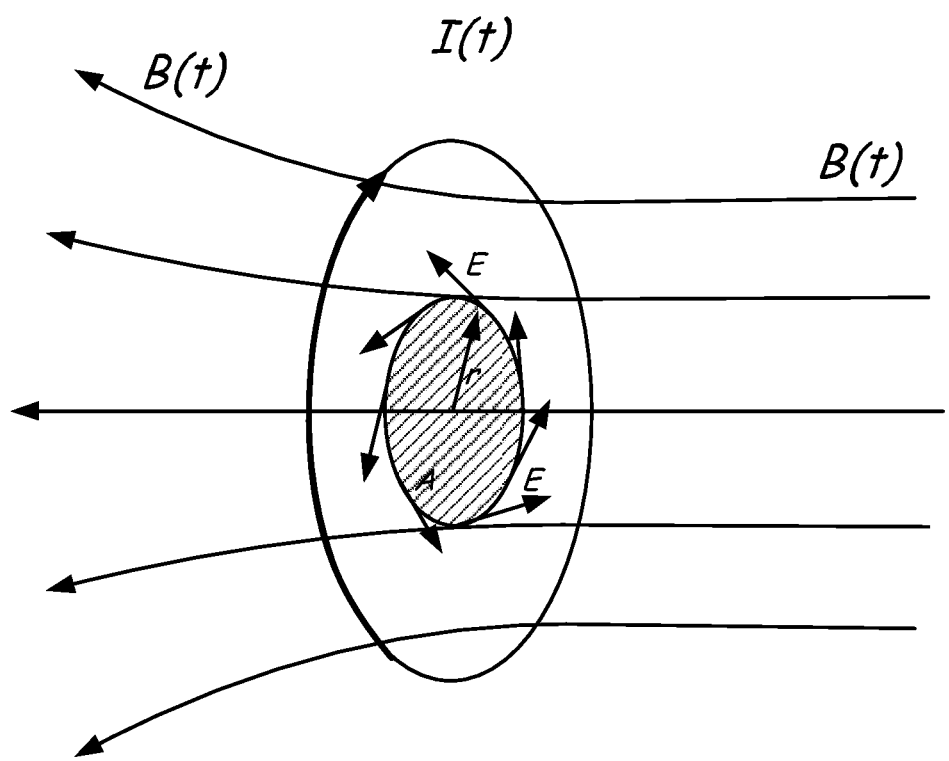
FIG. 2 is an illustration of the electric field E generated by a time varying magnetic field B(t) according to an example embodiment.

Generally, solution of the equation 9 requires computer simulation due to its complexity. In the case with axially symmetric coil for integration we can select a circular loop coaxial with the coil. If we additionally assume that the magnetic field is uniform inside the loop, we can integrate equation 9 analytically. Because of the axial symmetry of the coil, the electric field E is also axially symmetric and can be a function of radius r only. Remembering that, let us select for a contour of integration a circle of a radius r coaxial with the coil and lying in its plane, as shown in FIG. 2. Integration of the magnetic flux for the right side of the equation 9 can be performed over the area A which in one example is a disk with radius r, shown in the FIG. 2 as shadowed. Then we can write the equation 9 as follows:

$$2\pi r E = -\pi r^2 dB/dt \quad (10)$$

Substituting expression 8 for dB/dt into equation 10 we can get for E:

$$E = 0.5r(U/(ND^2(\ln(8D/d) - 7/4)))\exp(-t/\tau) \text{ and for } t=0 \quad (11)$$

$$E = 0.5rU/(ND^2(\ln(8D/d) - 7/4)) \quad (12)$$

As can be seen from the equation 12, the electric field is proportional to the distance from the axis of the coil r. Minimum electric field E=0 is at the axis of the coil where r=0 and the maximum electric field $E_{max}$ is achieved at r=D/2 of the coil:

$$E_{max} = 0.25 U/(ND(\ln(8D/d) - 7/4)) \quad (13)$$

It can be appreciated from equation 12 that a higher electric field E in a PEMF system can be achieved with higher voltages U, lower numbers of turns N and smaller diameters D of the coils. The use of a lower number of turns N to get a high electric field is counterintuitive to conventional thought process in the art because it is opposite to the desire to get high magnetic field in a DC coil. In the last case, as can be seen from equation $B=\mu_0 NI/D$, the higher number of turns, the higher the magnetic field B is.

Nevertheless it is an instructive result that can be used in optimization of the PEMF systems. In many conventional and prior systems, the number of turns used is in tens and hundreds, which is suboptimal as far as the electric field generation is concerned.

A low number of turns N can be beneficially used in PEMF applicators for different joints. Low number of turns means ranging from 1 to 10, preferably from 1 to 6 turns. In this range, the inductance of the coils varies from a fraction of one microHenry to about 10 microHenry and time of relaxation falls between 10 and 200 microseconds, which allows for pulse durations to be in the range of 5 to 50 microseconds.

By decreasing the number of turns or diameter of the coil for the increase of the electric field, we decrease also the duration of the electric pulses from about several hundred microseconds routinely used in conventional devices to 5 to 50 microseconds. Keeping in mind that for being efficient, a PEMF system optimally provides long enough overall time of application of the electric field to the treatment volume. Said another way, if we want to gain a higher electric field by shortening the electric pulses, to compensate for that we have to increase their repetition rate. In previous art, as far as the pulse repetition rates in PEMF systems are concerned, a wide range from a fraction of one Hertz to hundreds of Hertz had conventionally been employed. Repetition rates up to several tens of Hertz were preferred at earlier times because they imitated temporary patterns of real time movements of the joints. It turned out not to be that crucial and the repetition rates up to tens of kilohertz were successfully employed. In our case, short pulses of duration 5 to 50 microseconds a repetition rate of several hundreds to several kilohertz may be appropriate.

If a coil having a low number of turns is made of a multistrand flexible wire, it is also flexible and provides another advantage over high multi-turn rigid coils: it is mechanically compatible with elastic fabrics and can be interwoven, applied, or sewn into or on them to form elastic-type applicators, for example, a "glove" applicator for the wrist and thumb, an elastic "knee hose" type applicator for treatment of the knee, or applicators for other joints in the body specially adapted or configured for those joints and their movements.

Aside of the temporal pattern of the electric field induced by a PEMF coil, another feature is its spatial distribution. Due to its axial symmetry, the coil can create in surrounding space only axially symmetric magnetic and electric fields. This fact is reflected in formula 12, in which the electric field E is described as dependent only on the distance r from the axis of the coil and is independent of the azimuthal position of the point of observation. The electric field is curly, it is directed tangentially to the circumference at its point, as shown in FIG. 2. Also, the electric field is equal to zero on the axis of the coil and is low in the volume around it. This is substantially different from the magnetic field, which is approximately uniform throughout the full cross section of the coil. It should be noted that in a considerable part of the volume inside and outside the coil along its axis the value E could be below the necessary therapeutical level. Therefore, no treatment occurs in this volume. It is a "no treatment zone" or "dead zone". If an arthritic lesion is located at the center axis of a single coil, it will not be treated. This particular feature of the electric field distribution in the PEMF coil has not been appreciated by persons having skill in this art and is not addressed in the designs of conventional PEMF systems.

Figure 3:
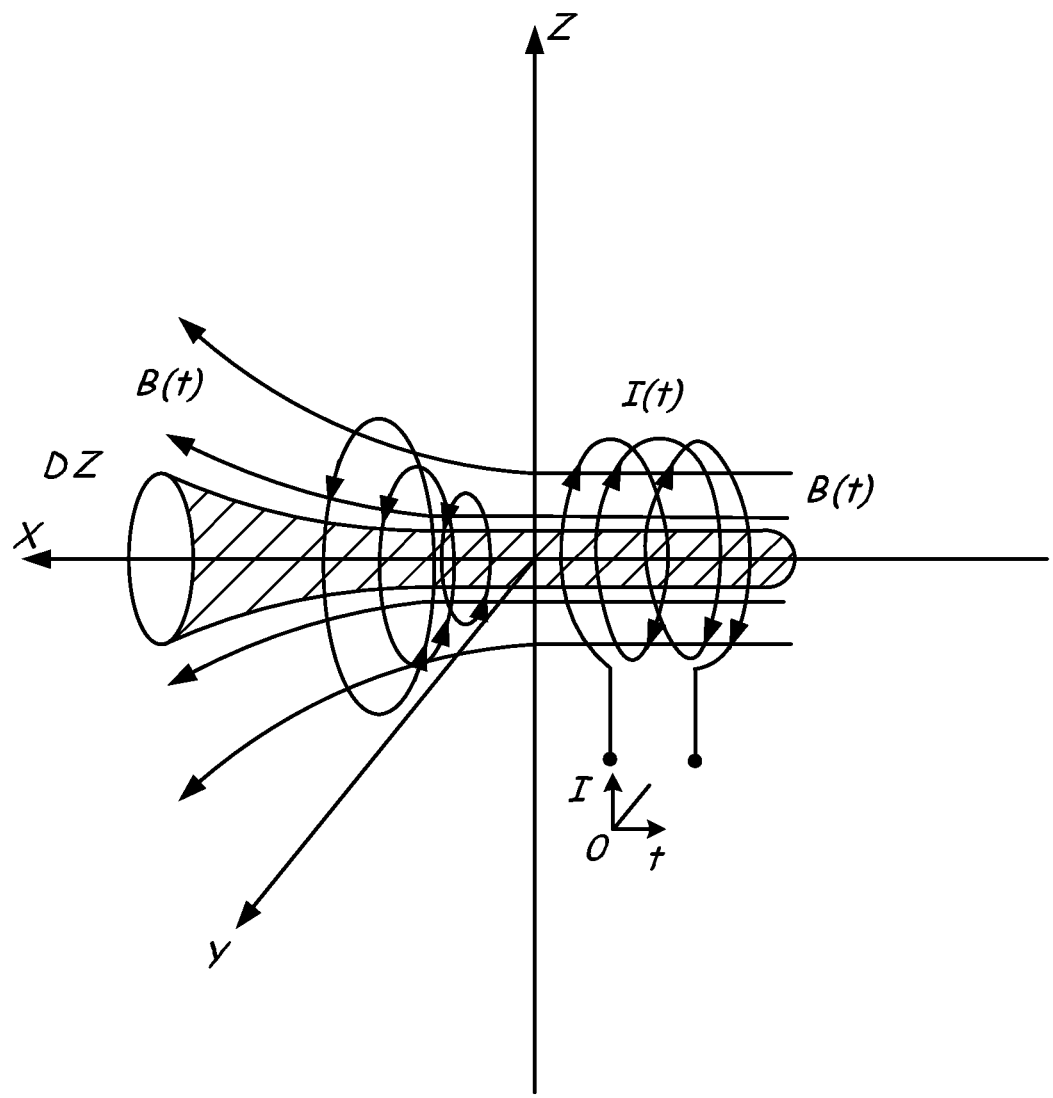
FIG. 3 is an illustration of a curl electric field E(t) produced by a varying magnetic field B(t) according to an example embodiment.

FIG. 3 schematically illustrates the coil with a pulse current I(t) and magnetic field B(t). A curl electric field E(t) is produced by the varying magnetic field B(t). In FIG. 3 there is a volume in and outside the coil in which electric field value is below the therapeutical level. Inside the coil the shape of the "dead zone" is close to cylindrical while outside it increases in diameter forming a funnel shape "dead zone". The shaded surface encompassing the dead zone is marked by letters Dz standing for a "dead zone".

Inside the coil the dead zone has a radius $r_{dz}$ that can be calculated from the formula 12 and the value of electric field $E_{min}$ below which the therapeutic effect is absent:

$$rz = 2(E_{min}/U)D^2 \ln((8D/d) - 7/4) \quad (14)$$

It can be shown that outside the coil the axial magnetic field and, hence, the induced electric field, decreases by factor $(1+(2x/D)^2)^{1.5}$ as compared with the field inside the coil. Here x is the axial distance from the coil to the point of observation. The radius of the dead zone outside the coil then will be $$r_{dz}(x) = 2((E_{min}/U)D^2 \ln((8D/d) - 7/4))(1+(2x/D)^2)^{1.5} \quad (15)$$

The dead zone diameter outside the coil along its axis increases almost three times at the distance from the coil equal to the radius of the coil. It can be significant, especially for the anatomical cases in which the coil can not be placed around the joint but must be placed on the patient skin adjacent to the joint. In this case the joint can be exposed to the electromagnetic field only at some axial distance from the coil.

The presence of a dead zone in the existing coil applicators is a significant drawback of the current PEMF systems.

In practical cases the dead zone can reach centimeters in diameter. It leaves untreated lesions in a noticeable part of the arthritic joints. The treatment does not occur right in the center of the coil where the magnetic field is close to its maximum.

Figure 4:
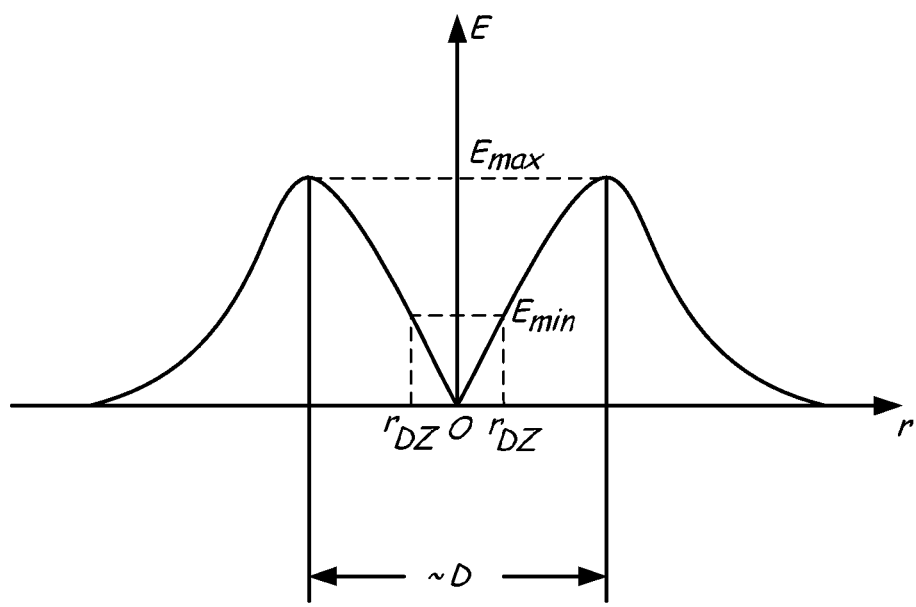
FIG. 4 is a qualitative diagram of cross sectional distribution of the absolute value of the electric field as function of a radial distance from the axis of the coil according to an example embodiment.

FIG. 4 shows a qualitative graph of cross sectional distribution of an absolute value of the electric field outside the coil as function of a radial distance from the axis of the coil. At the axis the electric field is zero and as the radius increases the electric field increases and reaches its off-axial maximum approximately at the radius equal to a half diameter of the coil, then it steadily fades away to lower values. Also, the radius of the dead zone $r_{dz}$, in which the electric field is less than the minimum therapeutic level Emin, is shown for low radii.

Figure 5:
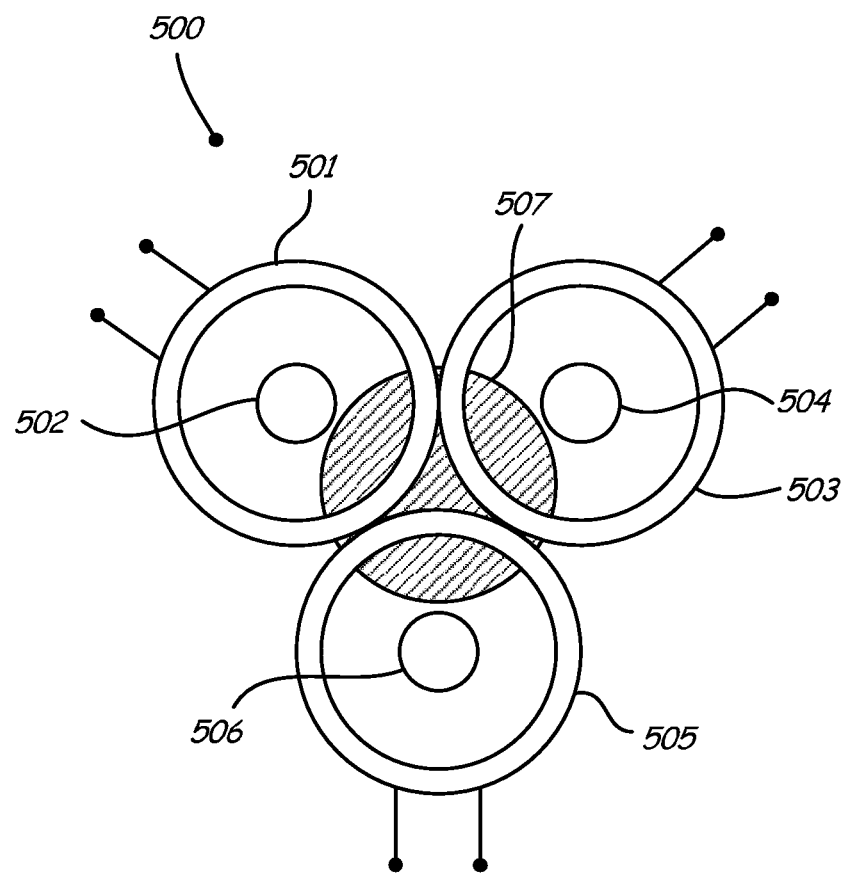
FIG. 5 is a schematics depiction of a PEMF applicator that is free of dead zones at the treatment volume according to an example embodiment.

As an example, FIG. 5 exhibits a schematic representation of a PEMF applicator free of dead zone at the treatment volume. In FIG. 5 numerals 501, 503 and 505 are designated to coils, numerals 502, 504 and 506 to their respective dead zones and numeral 507 designates the treatment volume. In the FIG. 5 the applicator is shown comprising 3 coils but it may be made of plurality of coils, such as 2, 4 or more coils. The axes of coils 501, 503 and 505 may be parallel as shown in FIG. 5, or coils may be arranged at different angles to each other. The individual dead zones of the coils are preferably outside the treatment volume or not overlapping in the cartilage volume. The diameters, the numbers of turns in the coils, the distance between them and their angular positions relatively to the joint are selected with this requirement in mind.

As mentioned before, the electric field of the coils reaches maximum value at a radial distance from the axis about a half diameter of the coil, so in the configuration shown in FIG. 5 where the coils 501, 503 and 505 are positioned close to each other, each coil produces at the center of the treatment volume 507 maximum electric field they are capable of generating. Sequential activation of all coils provides full coverage of the treatment volume 507 with the highest electric field achievable with each of the given coils. Activation of pairs of coils and all three coils simultaneously can also be performed. This kind of activation has a different spatial distribution of the electric field and provides maximum electric field closer to the margin of the treatment volume 507.

Improved coverage of the cartilage to be treated can be obtained by introducing activation of pairs of coils positioned in one plane but having opposite directions of the currents. As can be seen from FIG. 6, in this case the magnetic field B at the treatment volume is not axial, it is radial relatively to the coils, and is parallel to the plane of the coils ZY. The electric field lines E in the treatment volume are approximately parallel to the plane XY, which makes 90 degrees with the plane of the coils ZY. So, the contours of electric field lines, as compared with a one coil case, change direction by 90 degrees, providing a new spatial pattern of coverage of the treatment zone outlined by the dotted line. This particular combination of two coils with opposite currents is particularly suitable for the applications where the coils can not be positioned around the joint but should be secured outside the body, as in the case of the hip, shoulder or spine. Further in this application it will be disclosed how this configuration of coils can be used for PEMF treatment of the vertebral disks.

The design of the improved PEMF system disclosed herein can be further understood with regard to the following explanations.

It is generally accepted that the healing effect of the PEMF therapy is caused only by the electric field produced by a varying magnetic field. From the electric stand point, a biological cell consists of a conductive electrolyte surrounded by a dielectric lipid membrane. If a constant or low frequency electric field, such as used in conventional PEMF therapy, is applied to a cell over time about one microsecond or more, it is compensated by the movement of the ions inside the cell where electric field is reduced to zero. The difference of potential that was applied across the cell becomes applied only across the dielectric membrane. At the level of the electric field used in conventional PEMF, in the range of mV/cm, the lipid membrane stays intact, no pores are created in the membrane by the electric field, (no electroporation effect take place), and any electric current through the dielectric lipid membrane into the cell is impossible. The electric field inside the cell is zero. So, the electric field currently used in conventional PEMF therapy frequencies (tens of hertz to tens of kilohertz) cannot penetrate into the cell and, consequently, can not produce any effect on the nucleus, including gene transcription observed in PEMF therapy.

According to the improved PEMP therapy disclosed herein, during said PEMF therapy, the electric field produces currents in the soft tissues, such as in the cartilage, and causes bombardment of the chondrocytes membranes by ions present in the intercellular fluid. It is believed that the mechanism at work is ion bombardment via interactions with receptors on the surface of the membrane and ion channels through it sending a biological signal along an information pathway to the nucleus of the cell. These biological signals cause division of chondrocytes and DNA transcription in their nuclei that finally leads to production of the proteins, proteoglycans and other substances needed for repair of the cartilage.

Thus, from the preceding understanding of cartilage repair, it is not the magnetic field, even not the applied electric field that is the main agent producing the healing effect. It is the ion motion forced by the electric field in the intercellular space. If in some area of the cartilage there is no current, no healing effect is expected in such site.

In accordance with the Faraday's law of electromagnetic inductance, (equation 9) the curly electric field induced by a PEMF system in the tissue produces an electromotive force ∫Edl along any locked contour, magnetic flux through which varies in time. Whether it creates a current along the contour and how high will be the current is another issue. In a dielectric, even a relatively high electric field does not produce any current. But in a good conductor it will. The current induced by the PEMF system in a human joint depends not only on the induced electromotive force ∫Edl, but, in accordance with Ohm's law, also on the full electrical resistance along the contour.

If a contour crosses a layer of cartilage and a bone, electrical resistance of which is about 100 times higher than that of the cartilage, the current through this contour will be insignificantly low and no therapeutic effect is expected in the cartilage. Because the electrical resistivity of the bone is very high, actually only contours which do not cross a bone have a chance to carry a significant current. In the bulk of the bone, due to its high resistivity, practically there are no noticeable currents. It is only the contours passing through the cartilage tissue with its relatively low resistivity that carry the majority of the electric current. In other words, the electric current exists mainly in the cartilage layer and adjacent soft tissues. The current is especially high at a distance from the axis of coil where the electric field reaches its off-axial maximum, and where the "belt" of high current is created around the joint. At the same time the current almost does not exist in the segments of the joint where the cartilage layer crosses the "dead zone".

Humans have very sophisticated shapes of joints: ball-and-socket joints in shoulders and hips; hinge joints in fingers, knees, elbows, and toes; pivot joints in the neck and back; and ellipsoidal joints in the wrists. Therefore, it is very difficult, if possible at all, to cover the whole cartilage in a joint with one coil PEMF applicator. It is conceivable, though, creating an applicator that during operation moves from one position to another around the joint providing pulsed electric field from all directions. It is, probably, a good solution of the problem but it requires a relatively complicated piece of electromechanical equipment that can make the whole PEMF system significantly more expensive.

Another solution is to build around the joint an applicator comprising a plurality of coils which generate pulsed electromagnetic field to cover the joint from multiple places and directions. Arrangement or positioning of the coils at different places around and under different angles to the joint allows avoiding overlapping of the dead zones on the treatment volume. Such an applicator will create a plurality of different "belts' of current in the cartilage layer with different angular positions around the joint and can provide full coverage even for the most complicated joints. The coils may be activated in sequence one after another, or in combinations of two or more coils simultaneously. Also, to create a different pattern of distribution of the electric field, directions of the currents in some coils may be switched in different pulses to the opposite direction.

In the currently available one coil applicators, only axial pulse magnetic field is used for the coverage of the treatment zone. But, it should be noted, that at some distance along the coil's axis a significant component of the magnetic field is being generated and is directed in the radial direction perpendicularly to the axis of coil. An improved PEMF device can be provided to efficiently use this radial component for generating pulsed magnetic field and the curly electric field in the geometric patterns that are not achievable with the axial field only. The usage of the radial component allows for building sophisticated patterns of the electric field to accommodate special anatomical geometry of the human joints. For example, for a PEMF treatment of the intervertebral disks the optimum position of a coil is around the vertebral column. In this position the pulsed magnetic field will be directed along the spine column and the electric field would be applied circumferentially along the disk. Because the intervertebral disks are hollow, the dead zone of the coil would not create any problem, it would be applied to the hollow part of the disk. So, the position around the vertebral column seems would be an ideal position for the coil. But, anatomically it is impossible.

Figure 6:
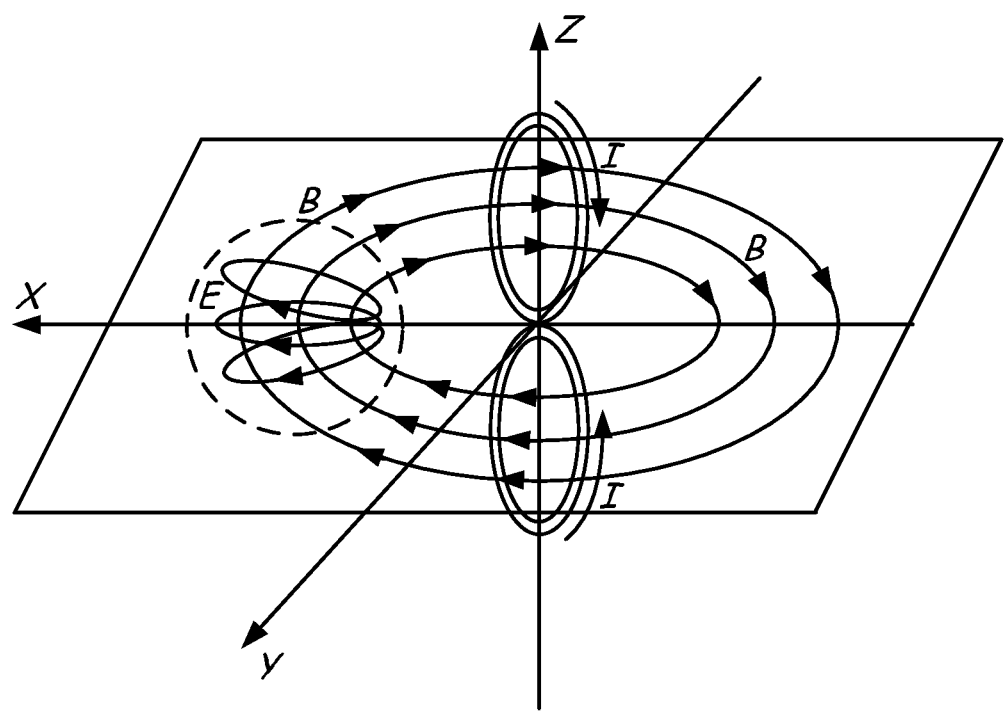
FIG. 6 is an illustration of the electric and magnetic fields of the applicator according to an example embodiment comprising two coils positioned in one plane and having electric currents in opposite directions.

FIG. 6, discussed above, demonstrates a combination of two coils that can create the electric field necessary for the treatment of the intervertebral disks. These two coils are positioned approximately flat in one plane on the back of the patient with their currents directed in opposite directions, clockwise and counterclockwise. Such a combination of coils creates a pattern of a curly electric field that is applied circumferentially along the whole body of the disk with the highest electric field at the outside edge of the disk where it is most needed because that is where the majority of injuries occur.

Temperature of the joint during PEMF treatment is also a factor in treatment efficacy. Articular cartilage does not have its own blood circulation and its temperature is less than the body temperature. During exercises, for example running or fast walking, the temperature of the cartilage of working joints increases up to 2-3 degrees C. This elevated temperature gives a boost to metabolism of the joints. Diffusion of nutrients from the blood to the synovial fluid and to the cartilage as well as diffusion of the waste products from the cartilage back to the blood stream increases noticeably. During physical activity, endogenous electrical pulses are applied to the cartilage and cause stimulation of its repair mechanism. It is known that arthritis of knee and hip joints can be reversed to a significant degree by long walking exercises of the joints. Thus elevated temperature of the cartilage is a factor in the repair process. However, conventional PEMF therapy routinely is used as a "cold" treatment, without any efforts to provide for elevation of the cartilage temperature.

In the article by Tatsuya Hojo et al "Effect of heat stimulation on viability and proteoglycan metabolism of cultured chondrocytes" (Journal of Orthopaedic Science (2003) 8: 396-399) the authors demonstrated that exposure of cultured chondrocytes to elevated temperatures 39° and 41° C. for 15 or 30 min had two profound effects on the cells. The first effect is the increased viability. As compared to control cultures kept at 37° C. the cells exposed to elevated temperatures had significantly higher number of survivors 72 hours after applying the heat stimulation. The second effect is increased proteoglycan metabolism. As compared to the control cells kept at 37° C., the cultured chondrocytes exposed to elevated temperatures had significantly higher level of proteoglycans found both inside and outside cells in the culture supernatant. It was found also that the cultured cells exposed to 43° C. and higher had both lower viability and metabolism.

In another publication, Hitoshi Tonomura et al (Journal of Orthopaedic Research (2008) 26: 34-41) demonstrated that the heat stimulation of rabbit articular cartilage in vivo caused increase in expression of extracellular matrix genes of proteoglycan core protein and type II collagen, the major structural components of the cartilage. It was discovered also that exposure of the cartilage to higher than 43° C. temperatures caused decrease in the gene expressions of proteoglycan core proteins and type II collagen and increase in expression of heat stress protein (HSP70) instead.

From the natural history of osteoarthritis it is known that the equilibrium in the cartilage turnover between the process of degradation of worn out extracellular matrix and rebuilding it with new proteoglycans and collagen II is tipped to the degradation by inability of chondrocytes to produce enough proteoglycans and collagen II—the major building blocks of the cartilage.

Heat stimulation of the joint increases blood flow around articular cartilage, promotes diffusion of the nutrients to the cartilage and removal of the waste products from the intercellular space between the cartilage cells. The waste products can be detrimental, even poisonous, especially from not completely healthy or dead cells, plenty of which are present in the joints affected by arthritis. Exposure to elevated temperatures cleans the environment and salvages a lot of compromised chondrocytes, which would die without it. Notably, heat increases viability of chondrocytes. By doing this it recruits significantly more cells for participation in the metabolic process triggered by PEMF and directed to the repair of the cartilage.

At elevated temperatures of 39-41° C., metabolism of chondrocytes is significantly higher than that at normal joint's temperatures. Thus, PEMF treatment applied to a joint at 39-41° C. will produce more proteoglycans and collagen II and will repair significantly more cartilage tissue than at normal joint's temperatures, which usually are even lower than a normal body temperature.

In one aspect, the present new osteoarthritis treatment method and device provide for a synergistic combination of heat stimulation and PEMF. The contribution of the heat stimulation to the effect of PEMF treatment on the cartilage is synergistic because, by changing metabolic rate of chondrocytes, elevated temperatures accelerate the process of DNA transcription and result in an increase in production of proteins and other substances needed for the cartilage repair.

As was mentioned before, the healing process in the cartilage is triggered by the electric current flowing in the intracellular space around the chondrocytes. When the temperature of the cartilage increases, so does the electrical conductivity of the intercellular fluid. If an electric field of the same magnitude is applied to a joint at elevated temperatures the current through the cartilage increases and, hence, the effect of the electric field on triggering the healing effect. It is an additional synergistic effect that heat stimulation exhibits on the efficiency of PEMF.

Another benefit of performing PEMF treatment at elevated temperature is the anesthetic effect. It is known from the "Gate theory" of pain that pain and heat signals from peripheral sensors compete with each other for the entrance into the spine. The heat signal has higher priority for passing through the gate and effectively blocks the signal of a moderate pain from passing into the spine and further to the brain where perception of pain is formed. Blocking the pain creates relaxation and a comfortable feeling for the user. These qualities benefit acceptance by users of the new thermally assisted PEMF therapy and creates a positive preference versus "cold" or "not thermal" PEMF.

As has been mentioned before, one of the objectives of the current invention is to keep the joint at elevated temperatures to enhance therapeutic effect of the PEMF. The preferred temperature to hold the joint at is in the range of 38 to 41° C. It is undesirable to exceed 42° C., thereby overheating the joint. Elevation of temperature above 42° C. for a significant period of time can cause deterioration of the cartilage and produce more harm than good.

Figure 7:
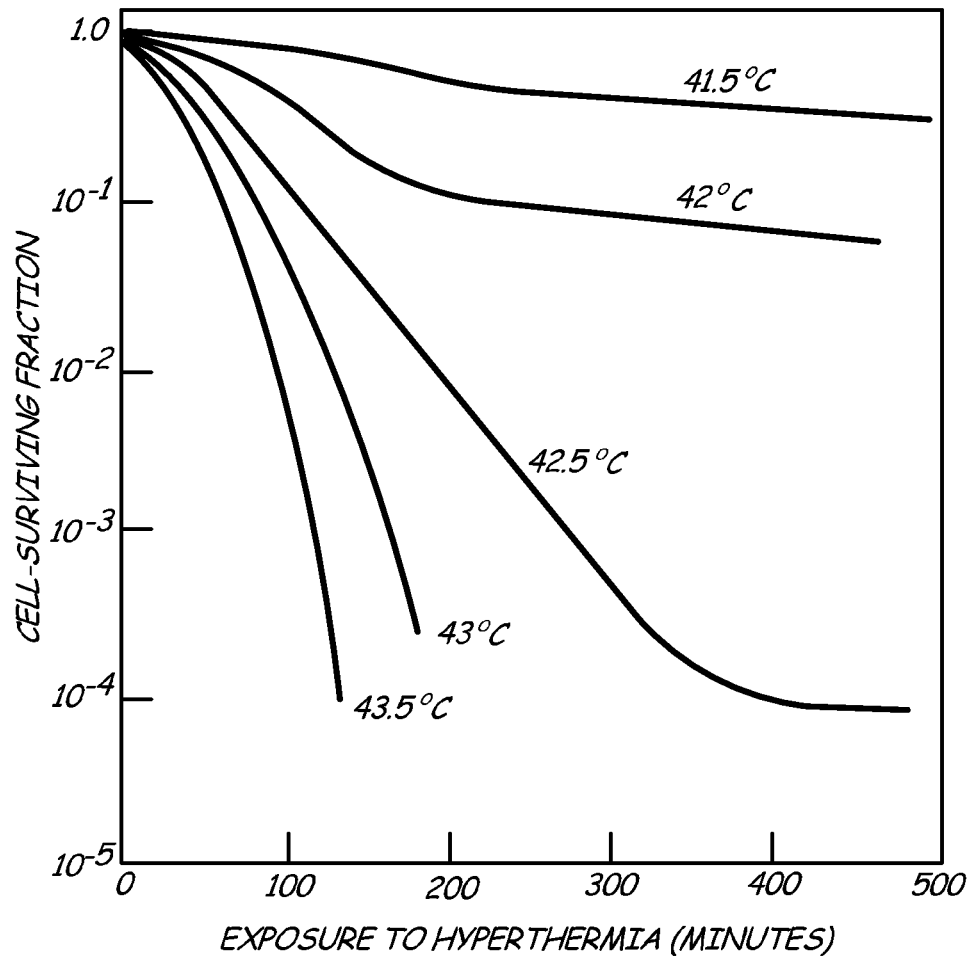
FIG. 7 is a graph of survival curves for a mammalian cell in culture heated at different temperatures for varying length of time.

It is known that survival of mammalian cells at elevated temperatures is characterized by both the temperature of the exposure and its duration. Different types of cells have slightly different tolerance to heat, but the basic pattern of cellular response to the heat treatment is similar. A typical graph of the survival of mammalian cells as function of time of the exposure for different temperatures is shown in FIG. 7. FIG. 7 presents a series of survival curves for cells exposed for various periods of time to a range of temperatures from 41.5° C. to 42.5° C. In our case the time of exposure is the treatment time, which is preferably between about 30 and 60 minutes, and most preferably between 30 to 45 minutes. However shorter and longer treatment times are within the scope of the invention.

As can be seen from the FIG. 7, in 1 hour time at temperatures 43° C. and above, the number of surviving cells decreases exponentially to a small fraction of their initial quantity. Below the temperature 41.5° C. all cells survive. Moreover, as has been demonstrated by Tatsuya Hojo et al., the vitality, or survivability, of the chondrocytes at 42° C. increase as compared to that of 37° C. Therefore, the preferred maximum acceptable temperature of exposure for a joint for a 45 minute PEMF treatment session according to the present invention is 42° C. The preferable and effective range of temperatures for a PEMF treatment session in the preferred time range according to the present invention is 39 to 42° C. However, other combinations of therapeutically effective temperatures and time ranges may be utilized without departing from the scope of the present invention.

The heat required for keeping the temperature of the joint at 39-42° C. can be generated by several methods. One example is to use the ohmic heat generated by the electromagnetic coils and free wheel diodes placed near or around the joint. In such embodiment, the PEMF applicator to be in thermal contact with the skin around the joint. A layer of a material with significant thermal conductivity can be placed between the coils and the skin to spread the heat from the wires of the coils and the free wheel diodes to the joint and prevent local overheating under the wires and the diodes. For better heat transfer from a coil to the joint, the coils and the free wheel diodes may also be imbedded in pads made of ceramics or a potting compound. These pads will serve as thermal bridges between the coils and the joint and can be called heating pads. It is desirable for the ceramics of the pads to have a high thermal conductivity. This requirement is met, for example, by magnesium or beryllium oxides based ceramics. Silicone RTV may be used as a potting compound for flexible applicators. However other materials may be used that met these property goals without departing from the scope of the invention.

Figure 8A:
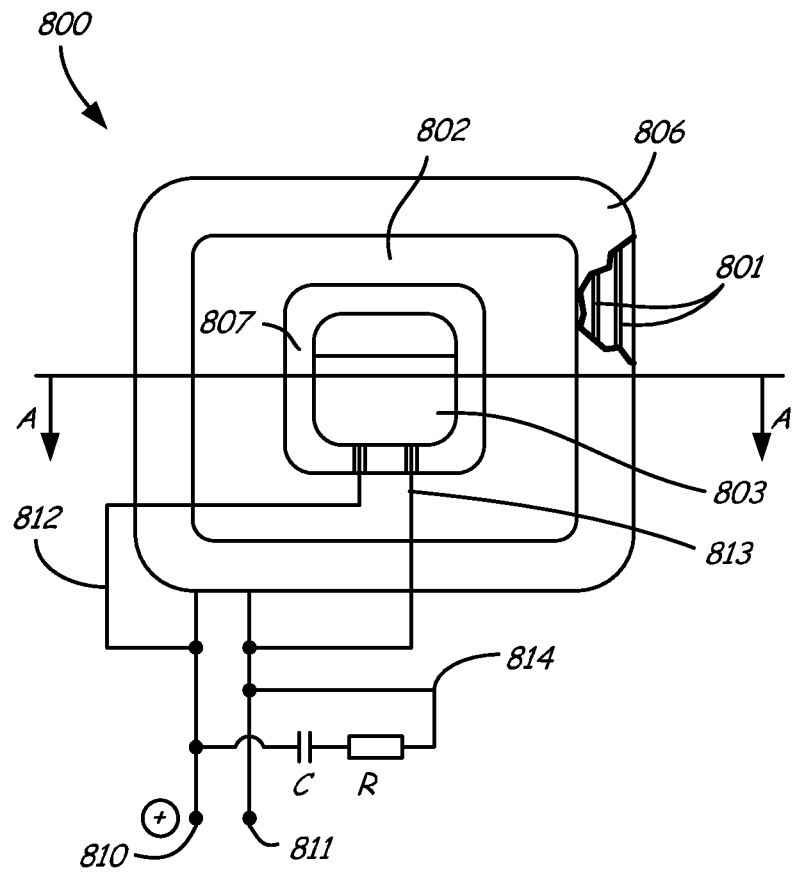
FIG. 8a is a top view and FIG. 8b is a side sectional view of schematic representations of a heating pad comprising a coil, a free wheel diode and a ceramic heat sink according to an example embodiment.
Figure 8B:
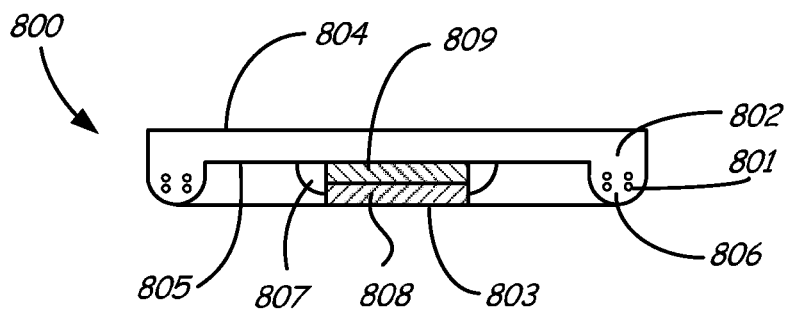

An example implementation of the heating pad is shown in FIGS. 8a and 8b. FIG. 8a shows a front view of the pad and FIG. 8b shows a cross section view of the pad along the line A-A. The heating pad 800 includes a several turn coil 801, a ceramic plate 802 and a free wheel diode 803. Ceramic plate 802 has two surfaces, surface 804 that interfaces the patient and the opposite surface 805 on which coil 801 and free wheel diode 803 are secured. The coil 801 is secured to the plate 802 by a layer of ceramic adhesive 806 and free wheel diode 803 by a ceramic layer 807. Both ceramic plate and ceramic adhesive may be maid of magnesium oxide based ceramic similar to the adhesive Ceramabond 471 from Aremco Inc. However other materials may be used without departing from the scope of the invention. The free wheel diode 803 comprises of the diode itself 808 and its heat sink 809.

Ceramic adhesive has high thermal conductivity and provides a good thermal contact for the diode heat sink 809 with ceramic plate 802. Coil 801 is imbedded into ceramic adhesive and also is in a good thermal contact with the ceramic plate 802. In this embodiment of the PEMF applicator, all the heat generated in the coil and the free wheel diode is efficiently transferred to the ceramic plate 802. Numerals 810 and 811 designate the terminals of the coil positive and negative correspondently, negative end 811 being grounded. Numerals 812 and 813 designate the positive and negative terminal of the free wheel diode. They are connected to the terminals of the coil 801. RC filter 814, connected parallel to the coil, performs the function of damping of the high frequency oscillations that arise in the circuit when the current in the coil 801 is interrupted. RC filter 814 effectively suppress electromagnetic interference resulted from these oscillations.

During a pulse, when the coil is connected to the DC power supply, the energy delivered by the power supply is spent on the Ohmic heating of the coil and creating a magnetic field around it. At the end of the pulse, when the coil is cut off from the DC power supply, the magnetic energy induces an electric current in the circuit made by the coil and the free wheel diode. One function of the free wheel diode is to protect the circuitry from the high voltage surge which is created by the interruption of the current in the coil.

In the embodiment discussed herein, both the coil and the free wheel diode are in a good thermal contact with a ceramic heat sink. This allows not only to collect all the magnetic energy stored by the coil and use it for the heating of the treated joint, but also provides good cooling of the free wheel diode itself, which in turn, allows for achieving very high pulse currents.

To avoid overheating and better control the joint temperature during PEMF treatment, a temperature sensor or several of them may be placed on the applicator in the vicinity of the joint. Actual power delivered to the coils can be controlled by the pulse duration and/or its repetition rate or just switching the PEMF system on and off. When the temperature reading reaches the highest value determined by the patient or by the controller, the pulsing may be turned off completely, the pulse duration altered, the repetition rate be changed, or any combination thereof, to allow the applicator to cool down. The physiological feeling of comfortable warmth in the joint may also be used as an indication that the temperature is right and should not be increased or decreased.

A high frequency generator periodically connected to the electromagnetic coils can be used for the purpose of deep heating of the joints and keeping their temperatures elevated. In one implementation of the system with deep heating, PEMF applicators comprise two coils, the first being a PEMF coil with a free wheel diode and the second one coupled to a high frequency generator which is periodically energized to provide deep heating to the joint. The operating frequency of the generator may be about 10 megahertz or higher in the frequency range where the absorption of the tissue is high. The temperature of the coil applicator is measured by a sensor and provides a feedback to the controller for stabilizing the temperature at a desired level by decreasing or increasing the operating duty cycle of the high frequency generator.

Figure 9:
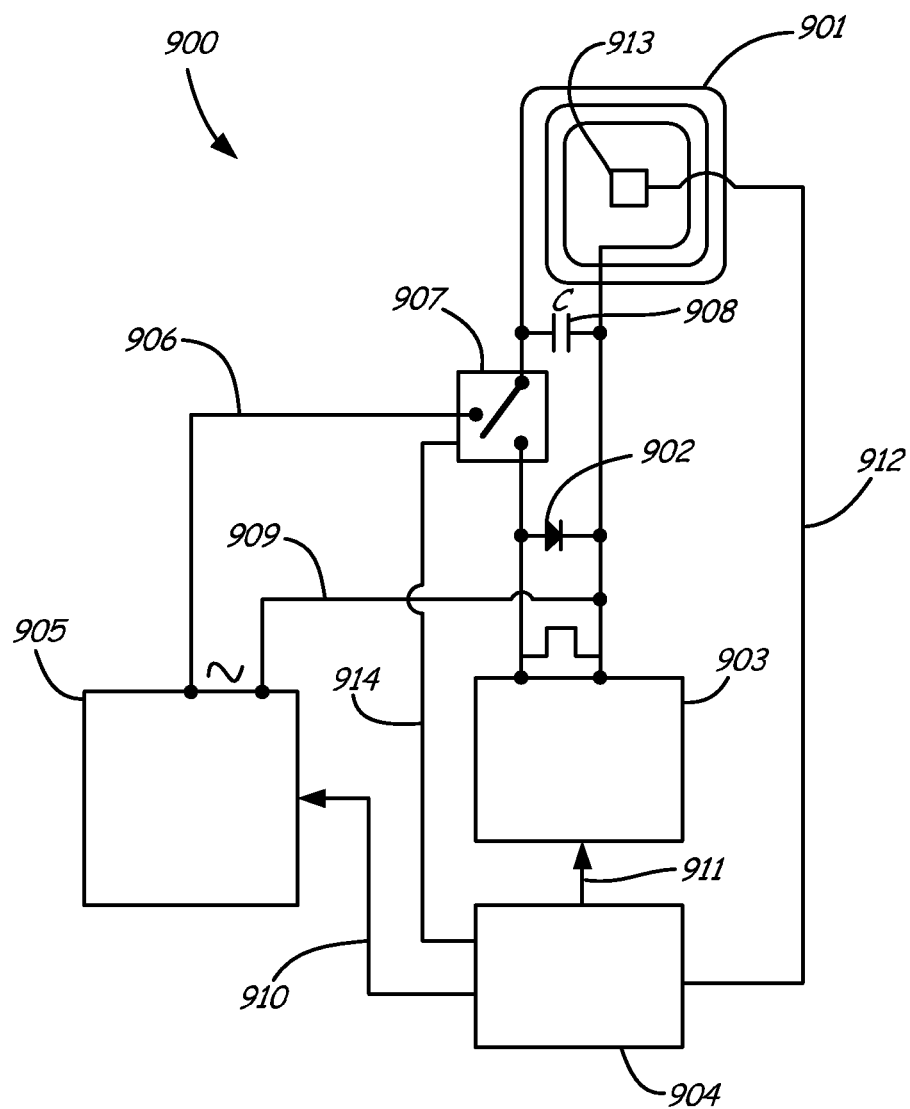
FIG. 9 is a schematic representation of a PEMF system with deep heating according to an example embodiment.

Another example embodiment of a novel deep heating PEMF system comprising a high frequency (HF) generator is shown in the FIG. 9. For simplicity of explanation, only one coil is shown in the PEMF system 900 depicted in FIG. 9. However it should be understood that the PEMF system 900 can comprise a plurality of coils. Numeral 901 designates an application coil with a free wheel diode 902 connected parallel to the coil 901. DC power supply 903 eclectically or functionally coupled with a controller 904 provides pulsed current to the coil 901 in a routine manner. A HF generator 905 operating in a megahertz range via a wire 906 and an electronic or electromechanical switch 907 periodically is connected to the coil 901. When the generator 905 is connected to the coil 901, the coil is disconnected from the DC power supply 903. The value of capacitor 908 connected parallel to the coil 901 is selected for the LC contour to be tuned in resonance with the frequency of the generator 905. The second output wire 909 of the generator 905 is grounded, as well as the negative pole of the DC power supply 903.

During operation of the system 900, signals from controller 904 via wires 910, 911 and 914 periodically connect to the coil 901, HF generator 905 or the DC power supply 903. When the DC power supply is connected to the coil, the system operates as PEMF. When HF generator 905 is connected the coil 901, the joint is heated by the high frequency electromagnetic field generated by the coil. To avoid overheating the joint its temperature is periodically measured by a temperature sensor 913. The reading from the temperature sensor 913 provides necessary feedback to the controller for stabilization of the temperature of the joint.

Now several alternative example PEMF systems with applicators for different parts of a human body will be discussed.

Figure 10:
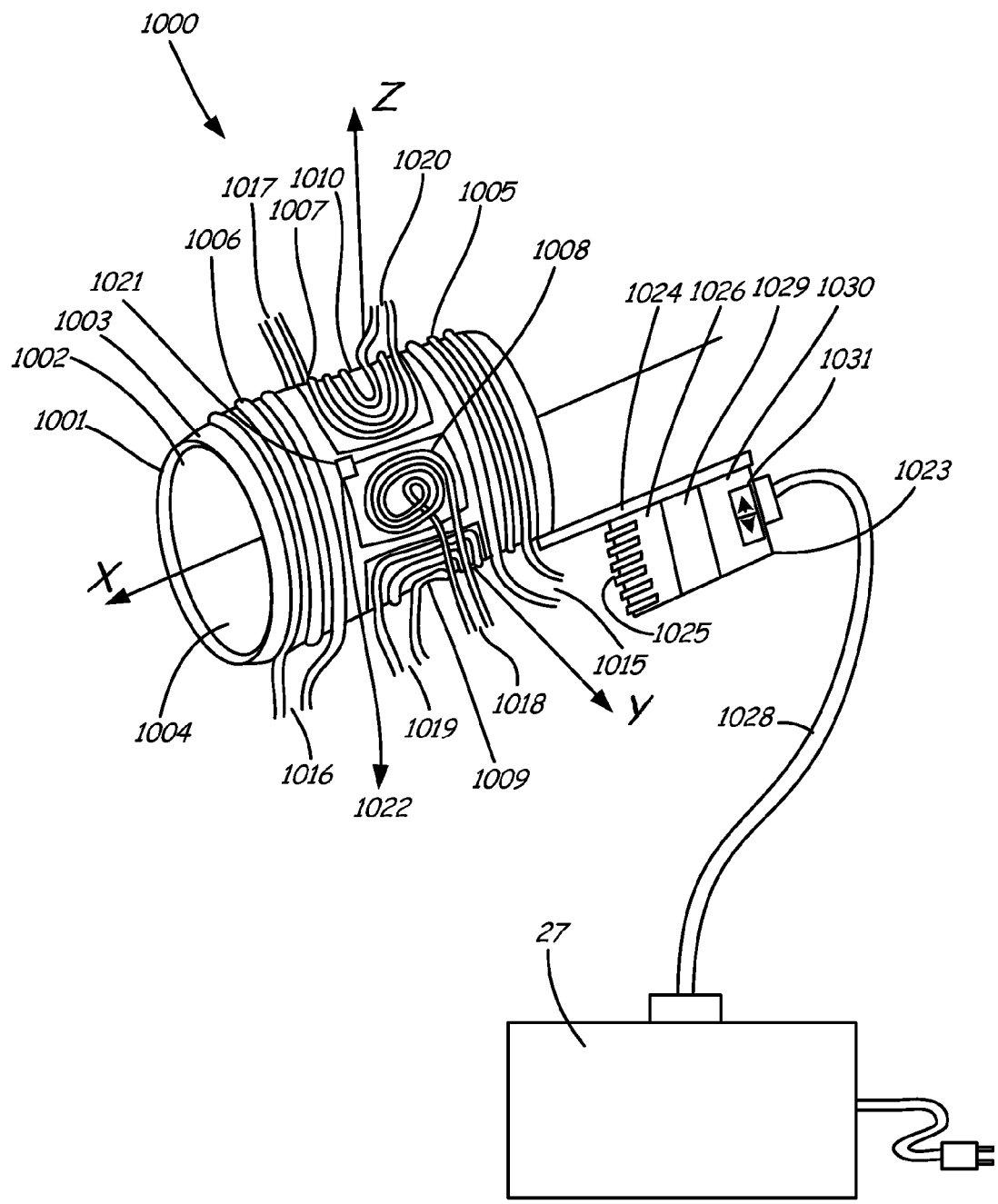
FIG. 10 is a PEMF system for treatment of arthritis of the hand including the wrist, fingers and the thumb according to an example embodiment.

The hand is one part of the human body that is very often affected by arthritis. All the joints in the wrist, fingers and the thumb can be affected. An embodiment of a PEMF system for treatment of arthritis of the hand, including fingers and the thumb, is shown in FIG. 10. The system 1000 comprises an applicator 1001 having a hollow core 1002, outside surface 1003, inside surface defining a hole or aperture 1004 and a plurality of electromagnetic coils 1005, 1006, 1007, 1008, 1009, 1010 secured on its outside surface 1003. An orthogonal system of coordinates XYZ, with axis X positioned along the axis of the applicator 1001 and axes Y and Z under 90 degrees to it, is shown in the FIG. 10.

Coils 1005 and 1006 are disposed or arranged around the hollow core 1002 at its opposite ends and are designated to generate magnetic field along the positive direction of the axis X. Coils 1007 and 1008 are positioned on the opposite sides of the applicator surface 1003 (coil 1007 is not visible in FIG. 10) to generate magnetic field along the positive direction of the axis Y; coils 1009 and 1010 generate magnetic field along the axis Z. In this embodiment a pair of coils are designated to generate magnetic field along each axis X, Y and Z. However, only one coil is shown in FIG. 10 for axis Y to simplify the drawing. Numeral 1015 designates the ends of the coil 1005, numeral 1016—ends of coil 1006, numeral 1017—ends of the coil 1007 and numeral 1018—ends of coil 1008, numeral 1019—ends of coil 1009; numeral 1020—ends of coil 1010. Also, on the surface of the applicator 1003 a temperature sensor 1021 with its ends 1022 is secured. A control unit 1023 via an intermediate member 1024 is attached to the applicator 1001. All ends of the coils 1015 through 1020 and the temperature sensor's ends 1022 are connected to a multi contact connector 1025.

In another embodiment, instead of two coils on each of axis Y and Z, only one coil on each axis can be employed or three coils positioned at 120 degrees around the applicator 1001. The magnetic field created by the coils inside the applicator 1001 may be substantially non-uniform. The electric field inside the applicator is higher than several mV/cm, preferably about 20 mV/cm.

The connector 1025 is a part of a switching board 1026 which comprises a plurality of "on-off" switches connecting the ends of the coils to a DC voltage. The DC voltage of 24 Volts is provided by a power supply 1027 to the control unit 1023 and to the switch board 1026 via cable 1028. The power supply 1027 itself is powered from an AC grid with a voltage of 110 Volts or 220 Volts.

The switch board 1026 is controlled by a processor 1029, which defines the sequence and duration of the connection of the coils to DC power supply and the repetition rate of the cycle. The control unit 1023 has a small display 1030 for displaying information, such as selected readings of the temperature sensor 1021. Control unit 1023 also has control buttons 1031 allowing to increase or decrease operating temperature of the applicator 1001. Alternatively, the control buttons can be provided as screen-actuated buttons on the display 1030. The change in the temperature of the applicator 1001 is achieved by changing the repetition rate of the cycle of the coil connections.

Figure 11:
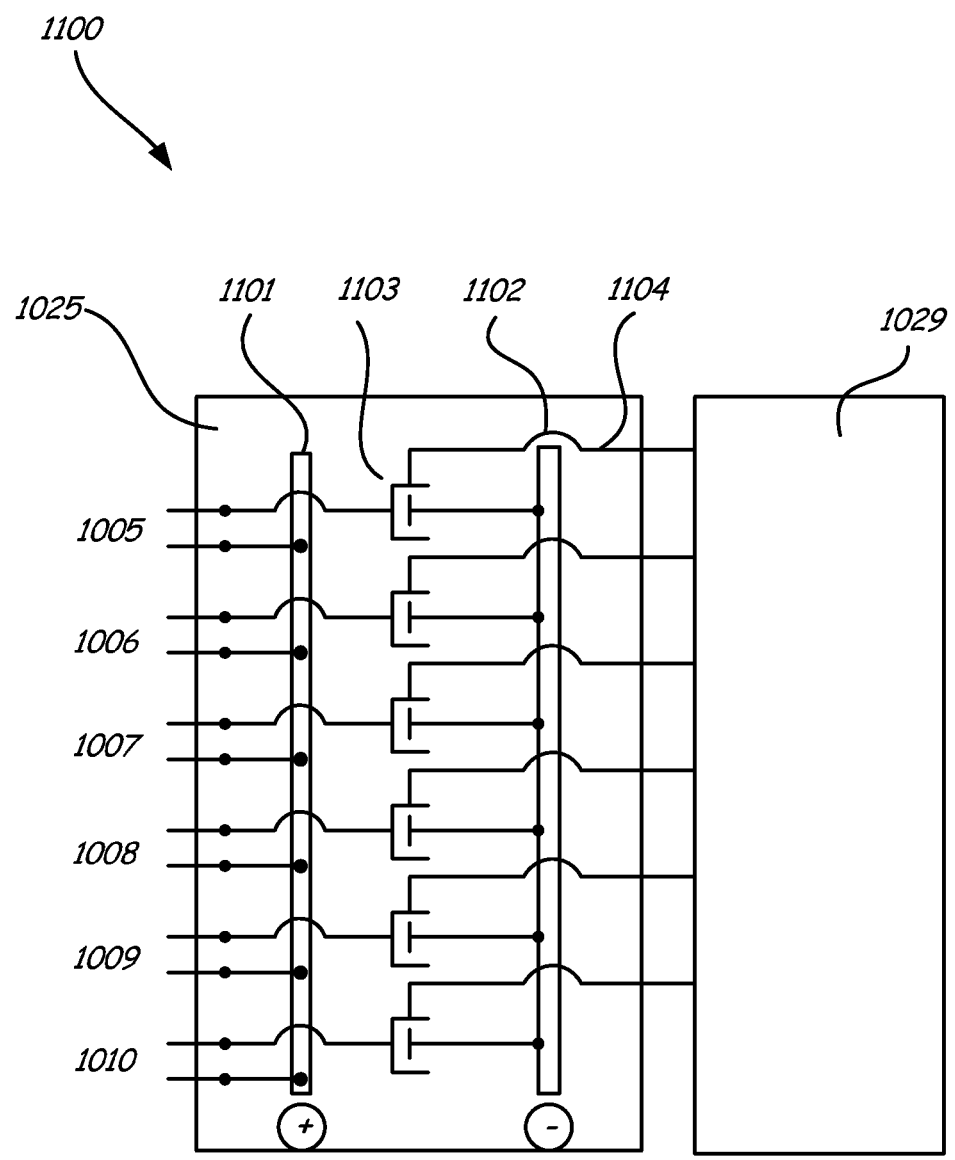
FIG. 11 is a schematic representation of a switching circuit according to an example embodiment.

In one embodiment of the switching board 1100, shown in FIG. 11, all 6 coils are connected to the DC power supply via a multi-contact connector 1025. One end of each coil 1005-1010 is directly connected to a positive pole 1001, while the other ends are connected to a negative pole 1102 indirectly, through a set of 6 high current switches 1103, one switch per end. A set of 6 controlling wires 1104 functionally connect the switches 1103 with a processor 1029. The processor generates signals defining states "on" or "off" of all 6 switches and runs the whole sequence of connections of the coils to the DC power supply. In this particular embodiment, all coils can be connected to the DC power supply parallel to each other, but serial or mixed connections also may be exercised in other embodiments.

The coils may be powered simultaneously in pairs, for example, 1005 and 1006 for creating a pulsed magnetic field along the axis X, 1007 and 1008 for creating a magnetic field along the axis Y and 1009 and 1010 for generating magnetic field along the axis Z. These pulsed magnetic fields create curly (rotary) electric fields around axes X, Y and Z and create electrical current belts in the cartilage layer of the joints. The direction of these currents follows the directions of the electric field in the cartilage with their central axes directed along the axes X, Y and Z.

Figure 12:
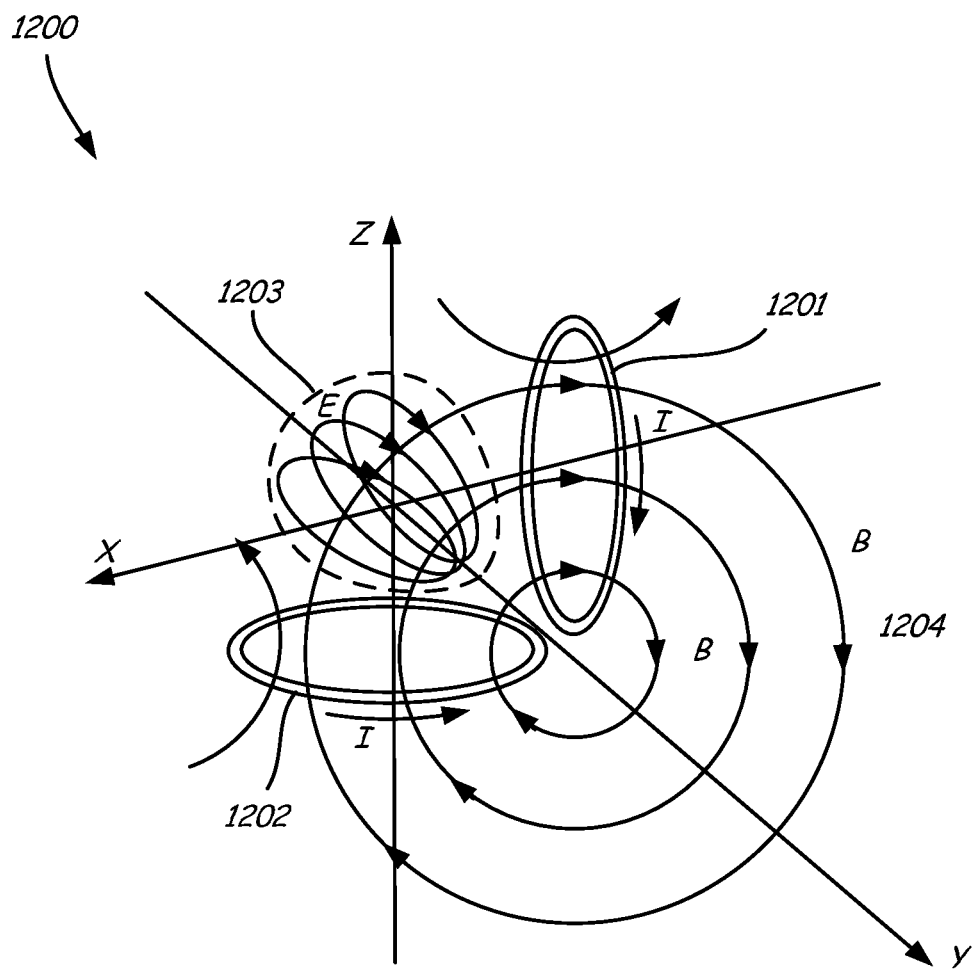
FIG. 12 is an illustration of electric and magnetic field of two coils at 90 degrees to each other.

Also, cross-axial pairs of coils can be powered in one pulse. In this case the coils positioned in the planes make 90 degrees with each other as shown in FIG. 12. Here a pair of coils 1201 and 1202 lay in planes making 90 degrees with each other. Coil 1201 generates magnetic field along the axis X, coil 1202—along the axis Z. They generate a pulsed magnetic field 1204 that is a vector sum of the magnetic field generated by each coil independently and, in FIG. 12, it is represented by circular loops passing through the interior of both coils 1201 and 1202. The pulsed magnetic field 1204 creates a curly non-uniform electric field 1203 that in the treatment zone lies in the plane that makes about 45 degrees with both axes of the coils. In the cartilage of the joint positioned in the treatment zone, a current belt is created with its axis turned about 45 degrees to the axes Y and Z.

In FIG. 10 two coils generate magnetic field along each axis X, Y and Z. The treatment zone is located at the center of applicator 1001 between the coils, so one of each pair of coils generates magnetic field directed in the treatment zone and the other—out of the treatment zone. In FIG. 10 all coils generating magnetic field directed in the treatment zone are designated with odd numbers: 1005, 1007, 1009 ("in" coils), while all coils generating magnetic field directed from the treatment zone are designated with even numbers: 1006, 1008 and 1010 ("out" coils).

For the most efficient generation of pulsed magnetic field in the treatment zone and hence the therapeutic electric field, for cross axial pulsing, "in" coils of one axis can be synchronously pulsed with "out" coils of another axis. In this combination, magnetic field from one coil will not partially compensate the magnetic field of the other coil and the resulting electrical field in the treatment zone will be maximal. All possible combination of "in" and "out" coils can be used for pulsing. Possible cross axial combinations of coils are: 1005-1008, 1005-1010, 1006-1007, 1006-1009, 1007-1010, 1008-1009, total 6. Three axial combinations for axes X, Y and Z make it total 9 combinations.

The PEMF applicator exhibited in FIG. 10 therefore provides curl electric field covering the treatment zone from nine different directions: along the axes X, Y, Z plus six directions making about 45 degrees with the axes X, Y, Z. In comparison with a one coil applicator the coverage of the joints with electric field is significantly improved. After a full cycle of nine pulses with different spatial distributions the applicator does not leave untreated any part of the cartilages of the wrist, fingers or the thumb.

Figure 13:
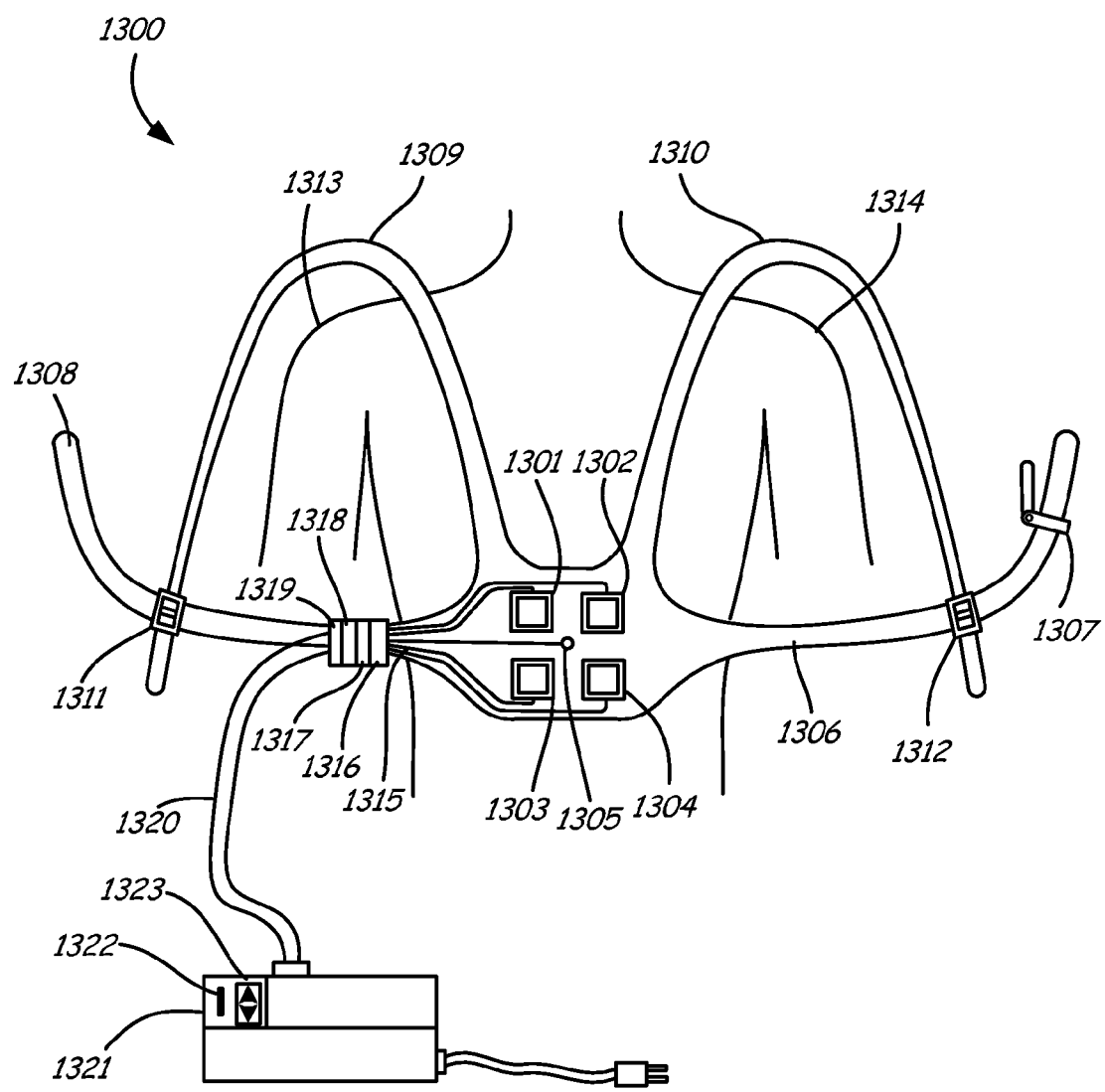
FIG. 13 is an illustration of a low back multi-coil PEMF applicator according to an example embodiment.

In FIG. 13, another embodiment of a multi-coil applicator 1300 of the present invention is exhibited. This embodiment is configured for treatment of the back pain. Back pain has two major origins: degeneration of the intervertebral discs and arthritis of the facet joints. The intervertebral disc is a cartilaginous structure that resembles articular cartilage in its biochemistry. The facet joints are located in the back portion of the spine. Two facet joints combine with the intervertebral disc to create a three-joint complex at each vertebral level. The facet joint consists of two opposing bony surfaces with cartilage on their surfaces and a capsule around them. The capsule produces synovial fluid to lubricate the joint. The facet joint arthritis causes inflammation and breakdown of the cartilage and results in stiffness and chronic or acute pain of the joint.

In FIG. 13, depicting the back applicator 1300, four PEMF coils 1301, 1302, 1303 and 1304 are disposed on a flexible belt 1306 to securably place the coils adjacent the patient's back. At the center of the back applicator 1300 a temperature sensor 1305 is also positioned. In another embodiment temperature sensors may be placed near each coil of the applicator. The belt 1306 has a buckle 1307 and the opposite free end 1308. Two harness strips 1309 and 1310 secured to the belt 1306 at its upper central part with first ends and the second ends engaged with buckles 1311 and 1312. The middle part of the harness strips go over the shoulders of the patient 1313 and 1014. The belt 1306 and the harness strips 1309 and 1310 allow positioning the four PEMF coils at a selected height and securing it against the treatment site. All wires 1315 from the coils and the temperature sensor connected to a multi contact connector 1316 which is a part of a switching board 1317.

In one embodiment the switching board 1317 includes a plurality of "on-off" switches to connect and disconnect the ends of all coils to and from positive and negative poles of a DC power supply to provide electric currents in the coils in clockwise and counterclockwise directions independently in all four coils. In this embodiment the switching board may have as many as 16 switches, two switches per one end of a coil for connecting to positive and negative poles of the DC power supply. The DC voltage, 12 or 24 Volts is provided by a power supply 1021 to processor 1318 and switch board 1317 via connector 1319 and cable 1320. The power supply 1321 itself is powered from normal household outlets, such as 120 or 220 Volts AC.

The switching board 1317 is controlled by a processor 1318 which defines the sequence, polarity, duration of the connections of all coils to the DC power supply and the repetition rate of the cycle. The processor 1318 is also functionally connected to the temperature sensor 1305. The temperature of the applicator selected by the patient is maintained by the processor 1318 via selection of the repetition rate of pulsing. Numeral 1322 is a display showing a selected temperature of the applicator. The display also has control buttons 1323 allowing to increase or decrease operating temperature of the applicator. Placing both the temperature display 1322 and control buttons 1323 in the power supply 1321 is optional; they can be as well placed in the processor 1318, on a remote control, or on the applicator.

Figure 14:
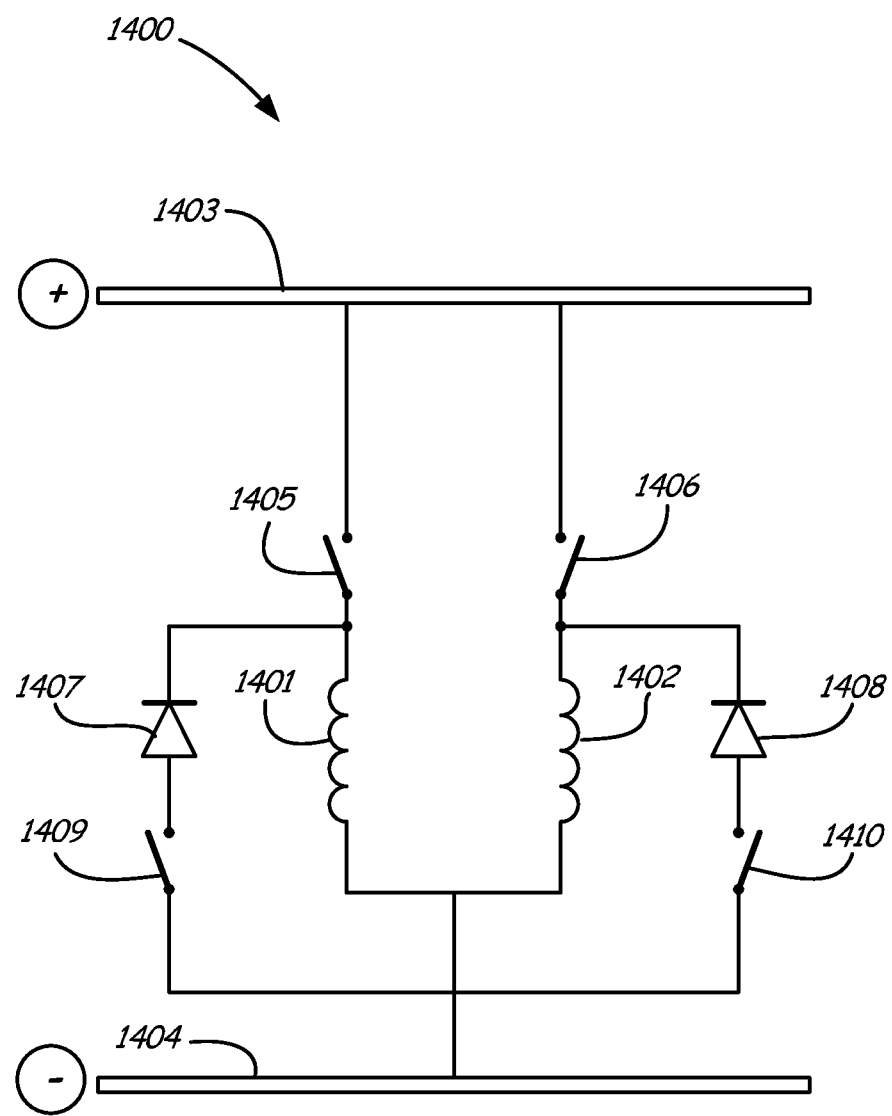
FIG. 14 is a schematic representation of two coils wound in opposite directions according to an example embodiment.

In a further embodiment of the applicator, instead of switching coils from one polarity to the other to change direction of the current in it, two coils wounded in opposite directions, clockwise and counterclockwise, can be used. The switchboard for this embodiment is schematically shown in FIG. 14. Here 1401 and 1402 are two coils with opposite windings; 1403 and 1404 are positive and negative poles of the DC power supply. High current switches 1405 and 1406 connect the coils one at a time to the positive pole 1403 for a preselected time of pulse. Because the opposite ends of the coils are connected permanently to the negative pole, every connection of a coil to the pole 1403 results in a current pulse through this coil. Coils 1401 and 1402 generate a magnetic field of opposite directions. Numerals 1407 and 1408 designate high current diodes which via switches 1409 and 1410 are connected to the ends of the coils. These diodes, called "free wheel" diodes, function to protect the circuitry from a transient high voltage peek arising at the ends of a coil when the current sharply collapses after disconnecting the coil from the power supply. The switch 1407 is turned into on-off states synchronously with the switch 1405, and respectively, switch 1410 is synchronized with the switch 1406. The energy of the magnetic field stored by the coils smoothly dissipates in the diodes 1407 and 1408 and the wires of the coils and the transient voltage peek in this case does not exceed a fraction of the DC voltage.

Figure 15:
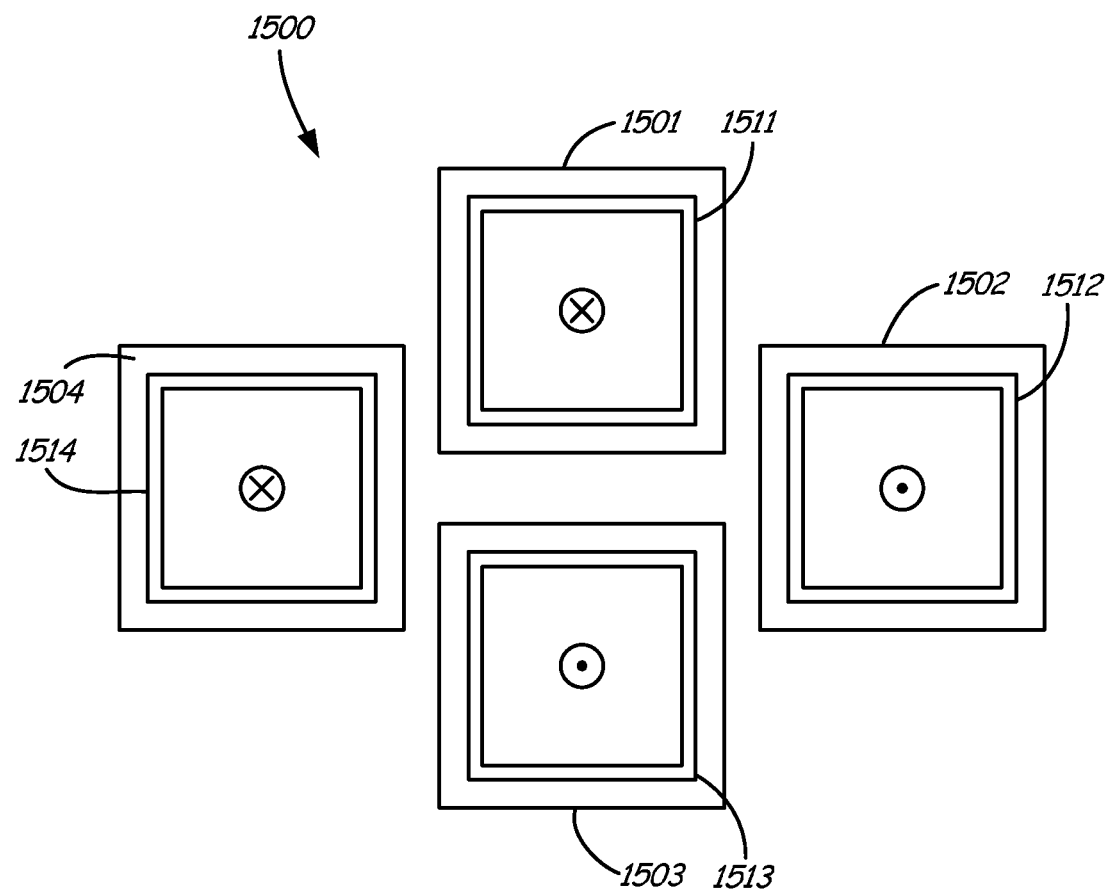
FIG. 15 is another example embodiment of a low back PEMF applicator.

FIG. 15 depicts yet another embodiment of the back applicator 1500. The coils 1511-1514 are shown attached to the ceramic pad 1501-1504. In this configuration, coils 1511 and 1513 are switched on simultaneously; they are intended for application of the curl electric field to the intervertebral disk. Coils 1512 and 1514 are intended for application of the curl electric field to the facet joints and are also switched together when the coils 1511 and 1513 are off. In this arrangement, the magnetic filed of coil 1514 is directed into the page while the magnetic field of coil 1512 is directed out of the page. Temperature sensors may be placed at each ceramic pad 1501-1504

Figure 16:
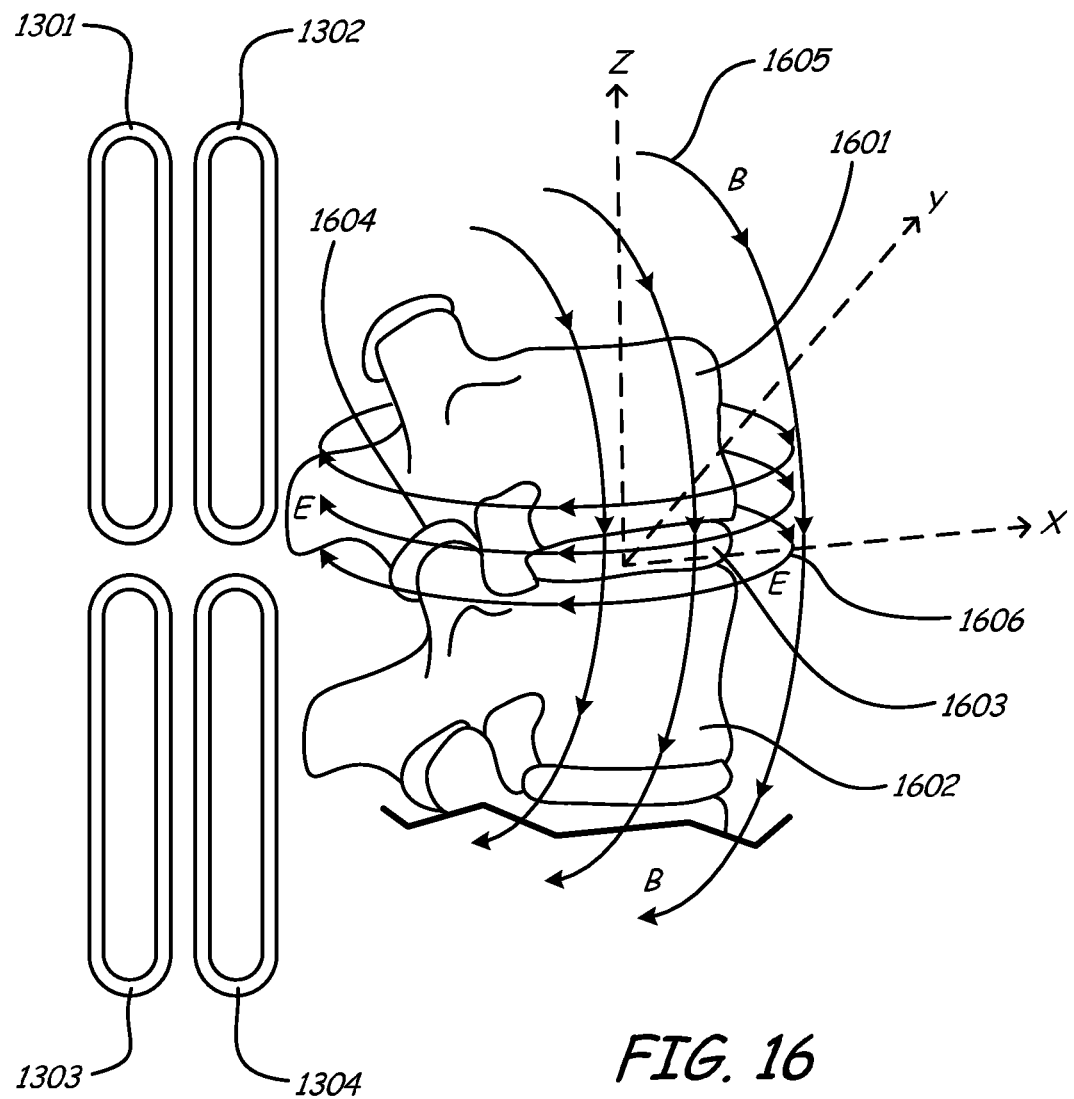
FIG. 16 is a schematic representation of electromagnetic field coverage of a human intervertebral disk and facet joints according to an example embodiment.

FIG. 16 schematically exhibits a segment of human spine 1600 and electromagnetic field covering an intervertebral disk and facet joints for the PEMF applicator shown in FIG. 13. Here 1301, 1302, 1303 and 1304 are coils of the PEMF applicator. During a pulse, coils 1301 and 1302 generate magnetic field in the direction of the spine and coils 1303 and 1304 in the opposite direction, from the spine. 1601 and 1602 are vertebras with intervertebral disk 1603 between them. 1604 is one of facet joints between the two vertebras; the second one, situated at the same level symmetrically with the joint 1604 is not seen in the figure. Magnetic field generated by the coils is shown on the segment of the spine with curve lines 1605. Curl electric field is shown by circular lines 1206. The electric field lines lie in the plane of the intervertebral disk 1203 and follow it circumferentially. Thus, the electric field configuration is optimized for the PEMF treatment.

Figure 17:
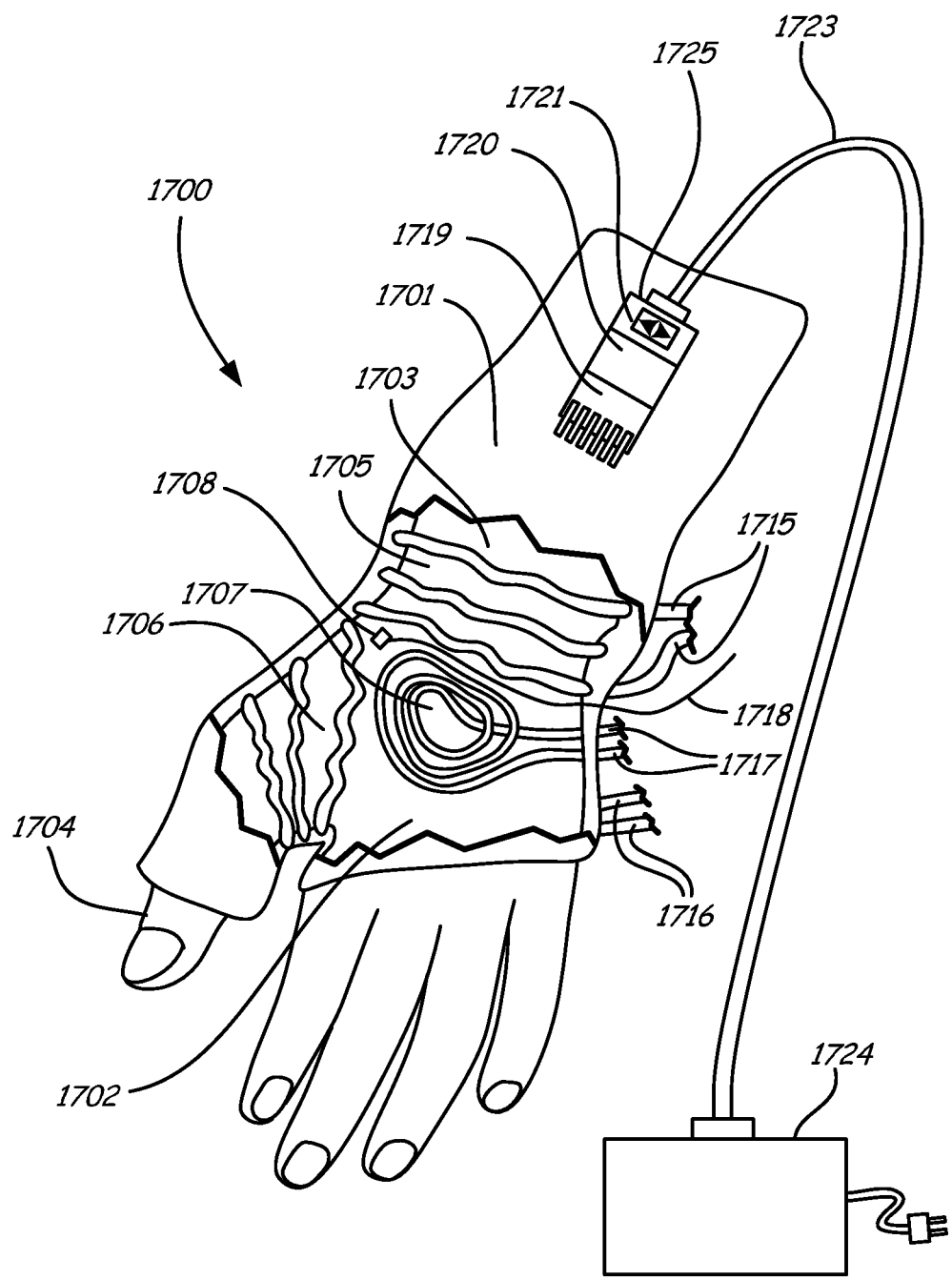
FIG. 17 is an illustration of a glove applicator according to an example embodiment.

FIG. 17 exhibits another embodiment of a PEMF applicator. The depicted open-fingered "glove" type applicator 1700 is configured for treatment of the wrist and thumb of the hand. The glove applicator 1700 includes or comprises two layers of elastic fabric 1701 and 1702 that cover the wrist 1703 and the thumb 1704 of the hand. The inner layer of the glove 1702 is seen in the cut-away portion of the upper layer that also exposes PEMF coils 1705, 1706 and 1707. Coil 1705 is wound around the wrist 1703; coil 1706 around the thumb 1704 and the coil 1707 is attached at the middle part of the back of the hand. A temperature sensor 1708 is disposed on the inner layer of the glove between the coils. Numeral 1715 designates the ends of the coil 1705; numeral 1716 designates the ends of the coil 1706; numeral 1717—the ends of the coil 1707 and numeral 1718 the ends of the temperature sensor 1708. The ends of all three coils and the temperature sensor are connected to a multi contact connector 1719 which is a part of the switching board 1720. The switching board 1720 is functionally connected to a processor 1721 which defines the sequence of pulsing of the coils. The switching board 1720 and processor 1721, via a cable 1723, are powered by DC power supply 1724. Processor 1721 has up-and-down buttons or knobs 1725 for selection by the patient higher or lower operating temperature of the applicator. Other patient input means, such as contact sensors or switches are also included within the scope of the invention.

While the coils can be actuated in any effective manner, the preferred sequence of activation of the coils is: single coil pulses though coils 1705, 1706 and 1707; double coil pulses trough coils 1705-1706, coils 1705-1707, and coils 1706-1707. In this case the coils 1705 and 1706 may be connected to the switching board 1720 as one direction coils.

In one preferred example, the magnetic field in coil 1705 is directed into the treatment zone and magnetic field in coil 1706—always out of the treatment zone. In their simultaneous pulse they deliver to the treatment zone a strong magnetic field that enters into the treatment zone through coil 1705 and leaves through the coil 1706. Coil 1707 is a two direction coil and is connected to the switching board 1720 with several switches, enabling controller 1721 to run the pulses in both directions and makes possible strong magnetic field pulses in both pairs 1705-1707 and 1706-1707. All coils of the applicator 1700 have low numbers of turns, generally less than ten, preferably 4-5 turns. For mechanical compatibility with elastic fabric the coils can be made of flexible multi strand conductors with diameters of the wires around 100-200 micrometers. Overall cross-section of a conductor is about 2-3 mm$^2$. In FIG. 17, some of the coils are shown as being "wavy." The waviness indicates elastic properties in the coils, including some spring action, so that they can be easily taken on and off the hand as part of the applicator.

Figure 18:
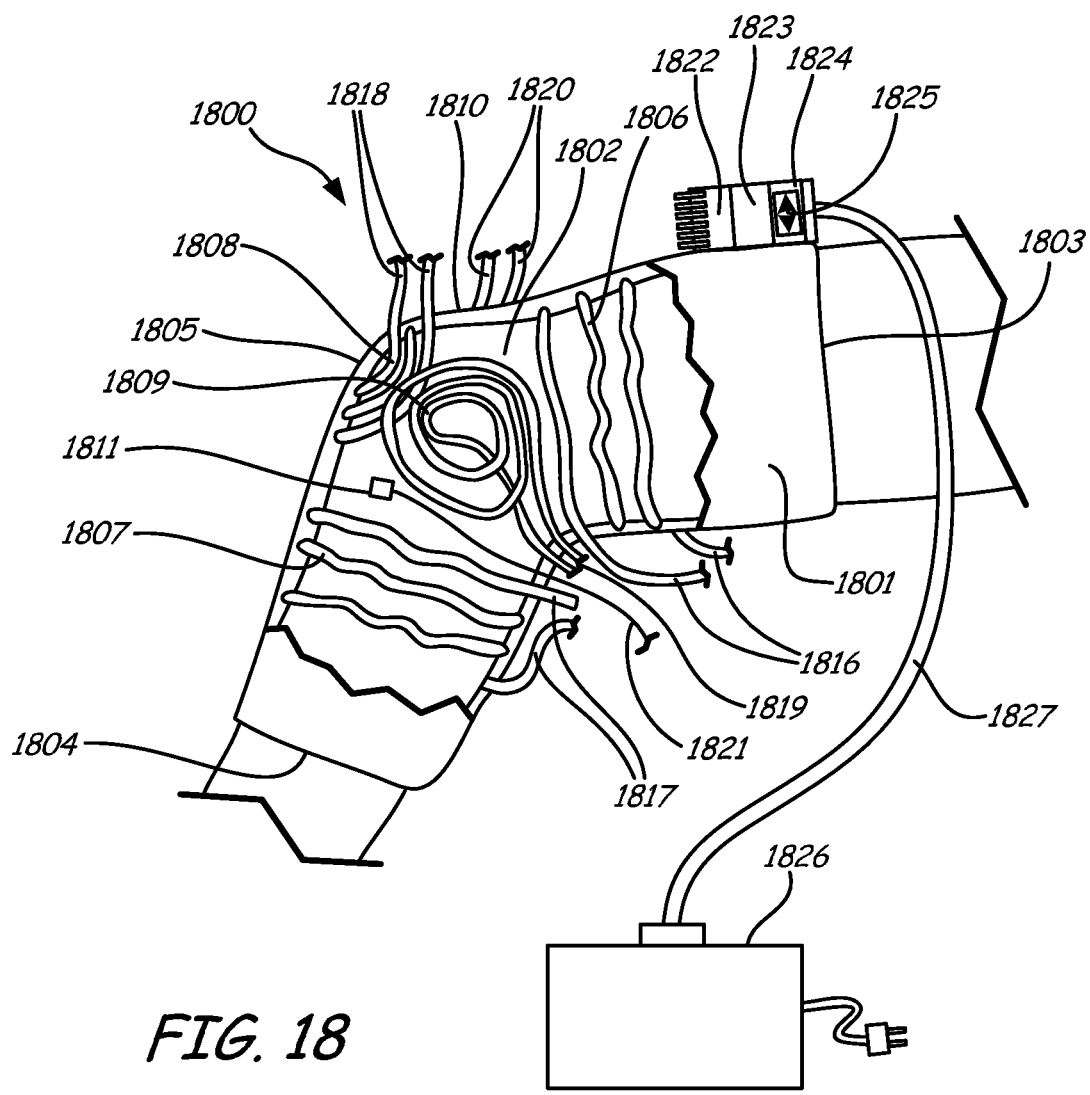
FIG. 18 is an illustration of a knee applicator according to an example embodiment.

FIG. 18 depicts a PEMF knee applicator 1800 according to a further embodiment of the invention. The applicator 1800 includes two layers of elastic fabric, the outer layer 1801 and inner layer 1802 which is seen in the cutaway portion of the outer layer. The upper end of the applicator 1803 is positioned above the knee 1805 and the lower end 1804 is below the knee 1805. Five PEMF coils are in the applicator 1800. However a larger or smaller number may be used.

Coil 1806 is wounded around the leg above the knee; coil 1807 below the knee; coil 1808 is placed around the patella of the knee and the coils 1809 and 1810 are at the right and left sides of the knee, coil 1810 is not seen in the FIG. 18. Numeral 1811 designates a temperature sensor positioned between the coils on the inner layer 1802 of the applicator. The ends of all five coils marked by numerals 1816, 1817, 1818, 1819, 1820 and the ends 1821 of temperature sensor are connected to a multi contact connector 1822 which is a part of, or is functionally connected to, a switching board 1823.

The switching board 1823 is controlled by a processor 1824, which defines the sequence of connecting ends of coils to a DC power supply 1826 and the repetition rate of the cycle. Processor 1824 has push up-and-down buttons 1825 that allow the patient selecting an operating temperature. However any other button, actuator or switch known to persons skilled in the art may be used. The operating temperature changes by changing repetition rate of the cycle or the duration of pulses in the coils. A DC power supply 1826, via a cable 1827, is connected to the processor 1824.

Multiple patterns of pulsing may be selected for the PEMF treatment of the knee with this applicator. Some coils, for example, coils 1806 and 1807 can be connected to a switching board as one direction coils, some coils can be connected as two direction coils, for example coils 1808,

1809, and 1810. A one direction coil 1904 with protective free wheel diodes can be connected to the DC power supply as shown in FIG. 19.

Figure 19:
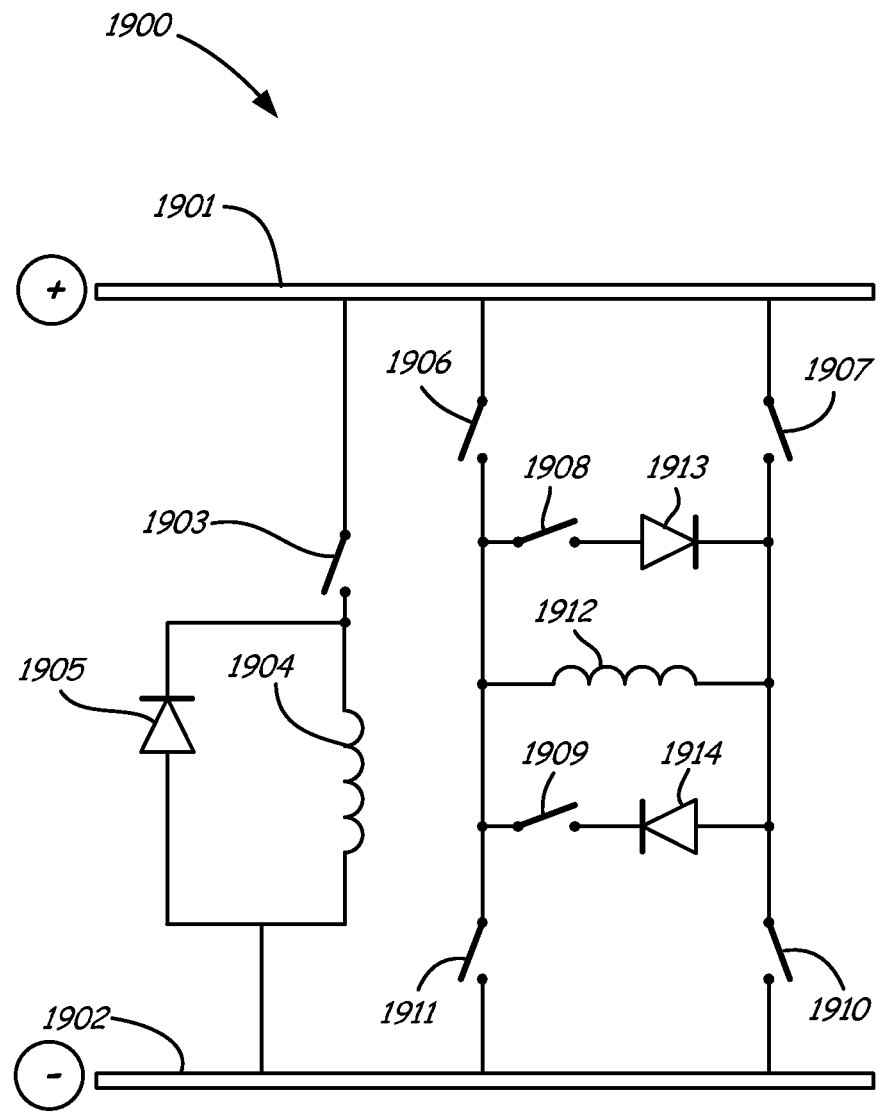
FIG. 19 is a schematic of one-directional and two-directional coils according to an example embodiment.

In FIG. 19 numerals 1901 and 1902 are positive and negative poles of the DC power supply; 1903 through 1911 are high current semiconductor switches, 1904 and 1912 are PEMF coils; 1905, 1913 and 1914 are protective free wheel diodes. The diodes function is to protect the electronic circuitry from a high voltage surge that takes place when the coil is disconnected from the DC power supply and its current collapses. A diode is connected parallel to the coil with its open direction against the DC voltage, so during the pulse there is no current in the diode. When the coil is disconnected from the power source, the current collapses and at the ends of the coil a high voltage surge of opposite direction appears due to the self inductance of the coil. The diode is then open for this direction and a current flows around the circuit made of the coil and the diode. If a protective diode is employed, the voltage on the coil during collapse of the current can be several times less than that of the DC power supply. When switches 1906, 1909 and 1910 are open and the rest of them are closed, coil 1912 generates magnetic field of one direction; when these switches are closed but switches 1907, 1908 and 1911 are open, the coil 1912 generates magnetic field in opposite direction. The two direction coil 1912 can be connected to the DC power supply as shown in FIG. 19. The two directional coils in one alternative embodiment may be made of two coils wounded in different directions (clockwise and counter clockwise) and connected to DC power supply as shown in FIG. 14.

Figure 20:
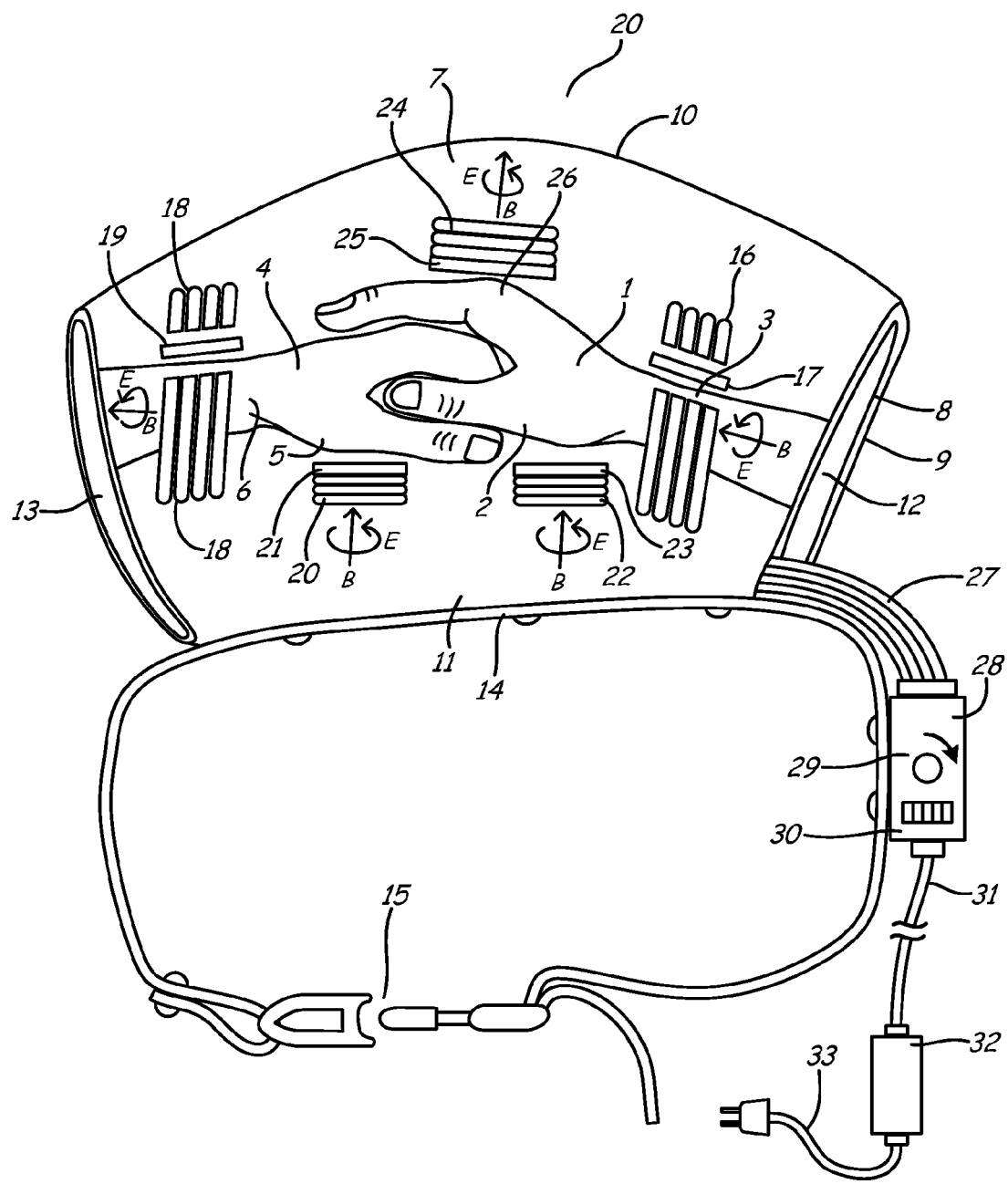
FIG. 20 is an illustration of a hand applicator according to an example embodiment.

Another implementation of a hand PEMF applicator is schematically shown in FIG. 20. Here are shown the right hand 1 with thumb 2 and wrist 3 and the left hand 4 with thumb 5 and wrist 6. Essentially cylindrical sleeve 7 of the applicator comprises at least two layers of fabric, inside 8 and outside 9 layers which are secured coaxially to each other. The sleeve 7 has front side 10 and rear side 11 and openings 12 and 13 for inserting right and left hands correspondently. The applicator 20 may have a belt 14, secured to the rear side 11 of the sleeve 7 and intended for attaching applicator 20 to the patient's waist by a buckle 15.

Between the layers 8 and 9 inside sleeve 7 a number of electromagnetic coils and heating pads are secured adjacent to the joints of the hands which frequently are subjects to osteoarthritis. Coil 16, made of very flexible multi strand wire, is secured between layers of fabric 8 and 9 around the right wrist 3; heating pad 17 is placed in a pocket between layers of fabric 8 and 9 in a vertical position in physical proximity to wrist 3. Similarly, coil 18 is secured around the left wrist 6 and heating pad 19 is placed adjacent to left wrist 6. Coil 20, encapsulated in a high thermal conductivity ceramics, is attached to heating pad 21 with a ceramic adhesive and positioned in a pocket on the rear side 11 of the sleeve 7 proximal to the left thumb joint 5. Coil 22 and heating pad 23 in a similar way are attached to each other and positioned at the right thumb joint correspondently. Coil 24 and heating pad 25 are placed near finger knuckles 26 in a pocket on the front side 10 of the sleeve 7. All wiring from the coils 16, 18, 20, 22, 24 and thermal sensors on all heating pads, not shown in FIG. 20, are combined in a cable 27 which is connected to the programmable controller 28.

Controller 28 provides pulsing currents into coils in a predetermined sequence in time and stabilizes the temperatures of the heating pads by changing repetition rate of the pulsing. Controller 28 is provided with a knob 29 for turning device on and off and selecting temperature of the heating pads. Display 30 provides information about selected temperature and the process of treatment. Cable 31 connects control unit 28 to a DC power supply which in turn is powered from AC grid by a cable 33.

Directions of magnetic field B and induced electric field E, provided by each coil, are schematically shown in FIG. 20 by straight and circular arrows. There are two phase of pulsing cycle in the device. In the first, coils 16 and 18 are powered simultaneously and provide magnetic field in direction along the hands. In the second, coils 20, 22 and 24 are powered and provide magnetic filed in direction perpendicular to the hands. Each cycle may have duration from several seconds to several tens of seconds. Duration of each individuals pulse may be from several tens of microseconds to several hundreds microseconds. Overall treatment time preferentially may vary from 0.5 to 1.0 hour.

Each coil has a protective "free wheel" diode connected in parallel to the coil and attached to corresponding heat pad by a high thermal conductivity ceramic adhesive. This feature of the design improves cooling of the "free wheel" diode and transports heat deposited in it to the heating pads.

Figure 21:
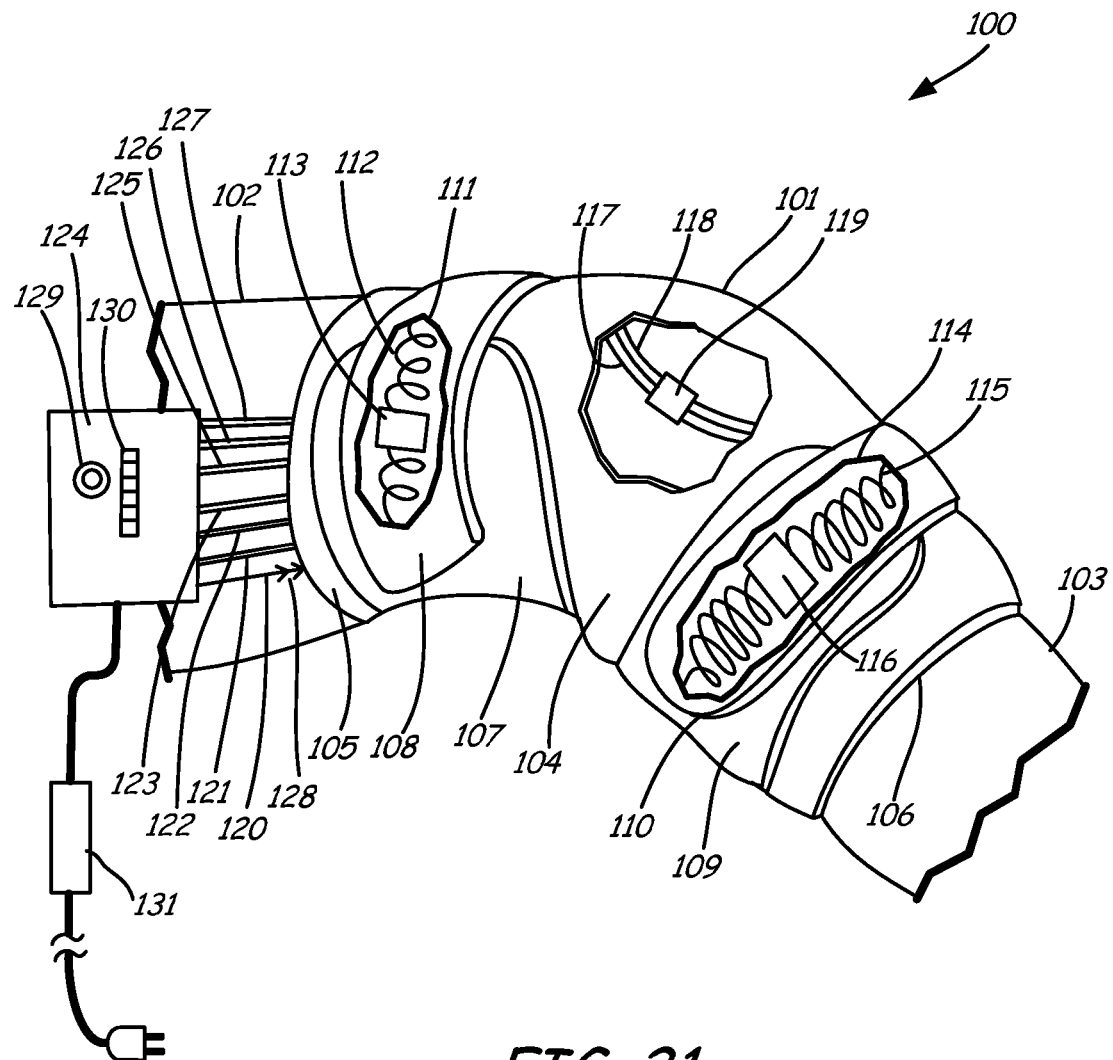
FIG. 21 is an illustration of a knee TA-PEMF applicator according to an example embodiment.

Referring to FIG. 21, knee applicator 100 comprises the body of the applicator 104 covering the knee 101 and stretching between the thigh 102 above the knee and the lower leg 103 below the knee. Numeral 105 designates the upper end of applicator and numeral 106—its lower end. Numeral 107 designates the upper wide belt; 108 is the upper narrow belt, both belts on the upper end of the applicator above the knee. The two belts wide 107 and narrow 108 secure the applicator 100 to the thigh 102 by a Velcro hook-and-loop fastener. However other suitable fasteners may be used.

The Velcro hook-and-loop fastener comprises two elongated fabric strips which are attached (sewn, adhered, etc) to the opposing surfaces between the belts 107 and 108, one of which contains multiple hooks and the other—loops. (Not shown in the FIG. 21). The low end of the applicator is secured over the low leg 103 by two belts 109 and 110 with two Velcro fasteners between them (not shown). In a cutoff 111 in the upper part of the applicator an electromagnetic coil 112 is schematically shown with a thermal sensor 113 secured to it, said thermal sensor is designated for monitoring the temperature of coil 112 and surrounding. The details of how the coil 112 and the thermal sensor are positioned in the applicator will be shown below in FIG. 22.

Similar to the upper end of the applicator, at the lower end in the cutoff 114 an electromagnetic coil 115 with a thermal sensor 116 secured to it. In the cutoff 117 a coil 118 and the thermal sensor 119 positioned at the knee patella (not shown) are schematically depicted. When activated, coil 112 above the knee applies a magnetic field along the thigh 102; the coil 115—along the lower leg 103 and the coil 118—perpendicular to the patella at the top of the knee.

Coils 112 and 115 are connected in parallel to another output of controller 124 via two high current wires 120 and 121. Coil 118 is connected to controller 124 via two high current wires 122 and 123. Thermal sensors 113, 116 and 119 communicate with controller 124 via double wires 125, 126 and 127. The wire 120 optionally may comprise a connector 128 which gives an opportunity to disconnect one end of coils 112 and 115 from a controller 124 and comfortably place the applicator 100 around the knee before treatment. For treatment, wire 120 is preferably reconnected to the coils 112 and 115 of the applicator. During wrapping the applicator around the knee, the connector 128 is preferably in a disconnected state. The disconnection of connector 128 allows performing placement of the applicator around the knee without creating an additional loop of high current wire 120 that can distort the electromagnetic field generated by coils 112 and 115.

Controller 124 includes a control knob 129 which turns on and off the PEMF system and allows selecting a treatment temperature of the applicator by the user. Light diode indicator 130 shows the elected temperature of the treatment. Controller 124 may be secured to a thigh or waist belt, not shown at the FIG. 21. Controller 124 is powered by a DC power supply 131 connected to an outlet of the power grid, or by other suitable power supply.

Figure 22:
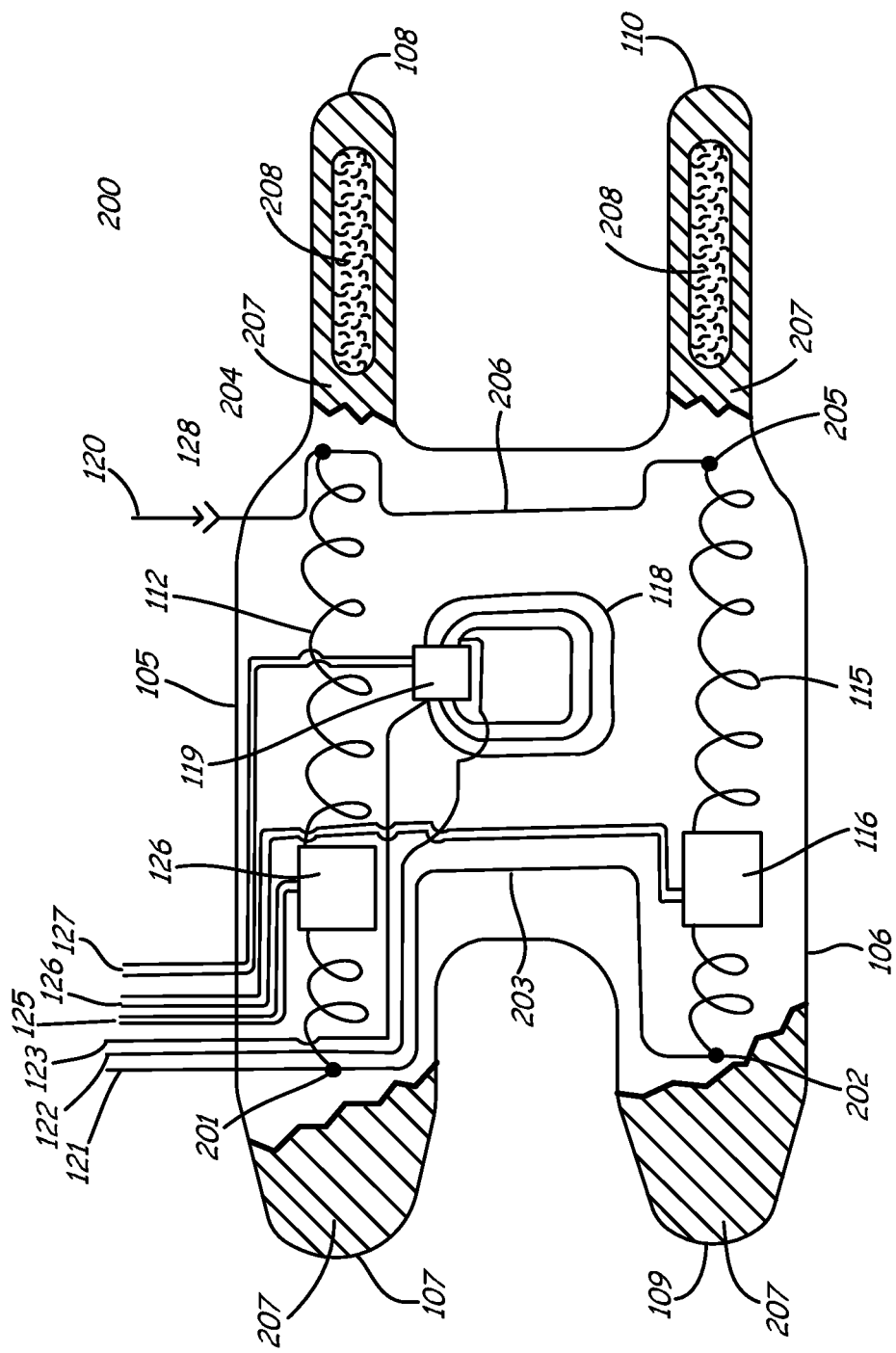
FIG. 22 is another illustration of a knee TA-PEMF applicator according to an example embodiment.

FIG. 22 schematically depicts the applicator 100 in an unwrapped state 200. All numerals in FIG. 22 that correspond to the parts visible in FIG. 21 are identical. New numerals in FIG. 22 are described below. Unwrapped applicator 200 is shown with a cut off in a fabric 207 covering inside surface of the applicator. Coil 112 at the upper part of the applicator has two ends 201 and 204. Coil 115 at the lower part of the applicator has two ends 202 and 205. These two coils are connected in parallel by a high current wire 203 which connects ends 201 and 202 and a high current wire 206 which connects ends 204 and 205. Wires 120 and 121 connect the parallel coils 112 and 115 to the controller 124 shown in FIG. 21. Wire 120 with connector 128 and wire 121 in FIG. 22 are depicted at the horizontally opposite ends of the applicator but after wrapping the applicator around the patient's knee the wires 120 and 121 will appear close to each other as shown in the FIG. 21. Numeral 208 designates two Velcro strips secured on the inner fabric layer 207 of two narrow belts 108 and 110. The matching Velcro strips that engage strips 208 in a wrapped around the knee applicator are attached to the external side of wide belts 107 and 109 and are not seen in FIG. 22.

Figure 23:
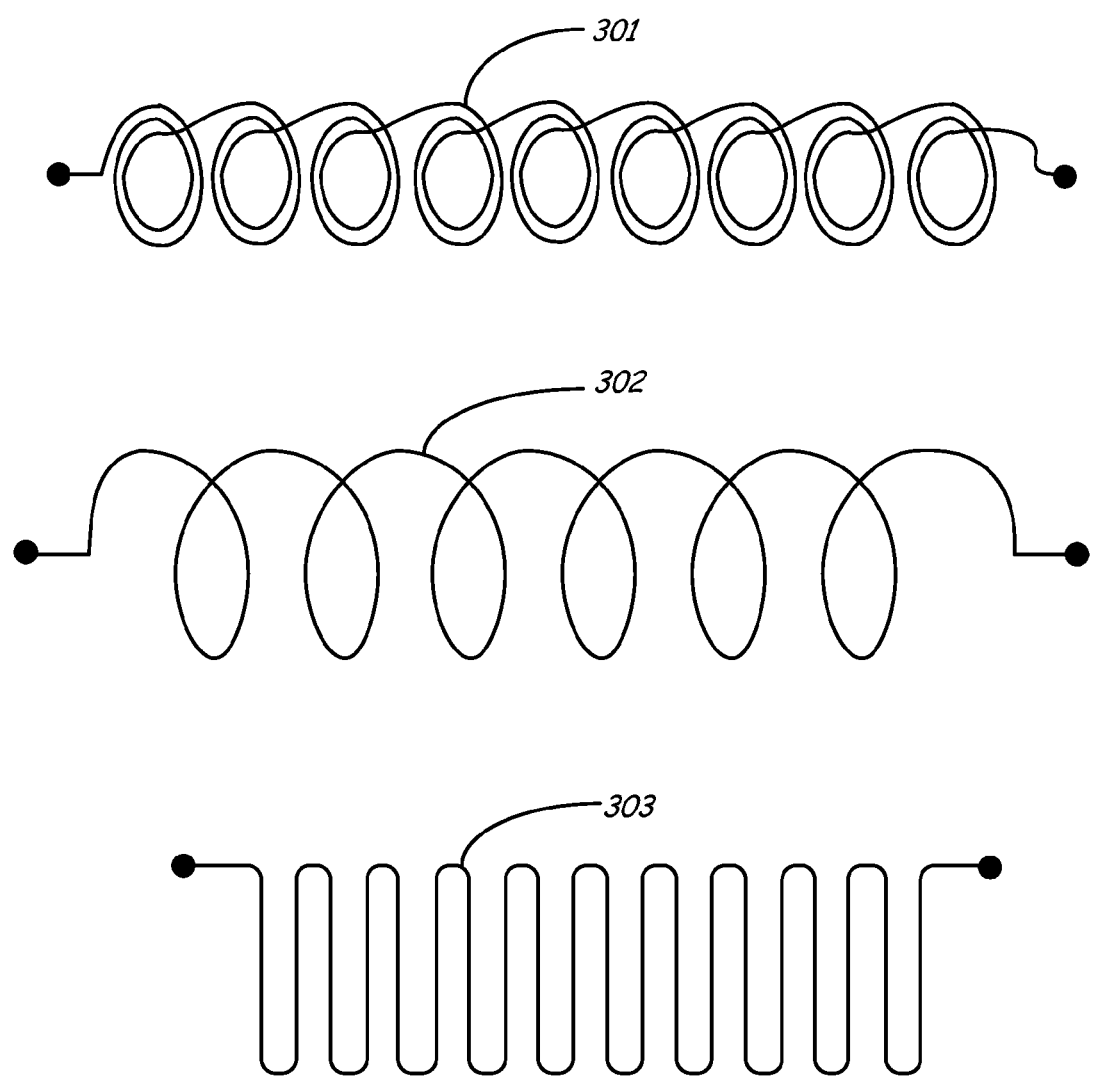
FIG. 23 is an illustration of coils for PEMF applicators according to example embodiments.

FIG. 23 illustrates certain different embodiments of coils 112 and 115 in an unwrapped state. All three embodiments 301, 302 and 303 are substantially flat in the plane of the drawing. Embodiment 301 is a chain of small coils having several turns each (exemplary 2 to 4) and connected serially. Embodiment 302 is a multi turn spiral flattened in the plane of the drawing. Embodiment 303 comprises a meander shaped wire. All three coils 301, 302 and 303 comprise high current solid or multistranded wires with the conductor diameter between 1 and 2 mm.

When a coil 301, 302 or 303 is wrapped circumferentially around a thigh or low leg it creates a magnetic field along its axis (and inside the knee volume) that is substantially equivalent to the magnetic field of a simple one turn coil made of a bent wire. Even though this simple one turn coil makes the knee applicator simple and easy to manufacture, it has a very low inductance (small fraction of a microHenry), which makes it very difficult to achieve electromagnetic pulses in the range of tens of microseconds, as desired by the PEMF treatment system.

All coils depicted in FIG. 23 comprise wires several times (e.g. three to five) longer than that of a simple one turn coil and have significantly higher inductance, in the range of 5 to 10 microHenry, which is sufficient for preferred duration of pulses in a PEMF system (20 to 50 microseconds). So, the higher inductance of the coils shown in FIG. 23 is advantageous in PEMF applicators as compared with applicators employing a simple one turn coil. Another advantage of the coils depicted in FIG. 23 is that they have significantly larger surface area that provides better conduction of ohmic heat generated in the coils to the treatment area versus simple one-turn coils.

When interrupted at the end of a pulse, the electric current through PEMF coils creates a very high spike of voltage between two ends of the coils. This spike can be as high as hundreds to thousands volts, and if not dealt with, it can damage the insulation of the coils and/or the controller of the system. As disclosed in U.S. patent application Ser. No. 12/878,028, this problem may be solved by adding a "free wheel" diode in parallel to the PEMF coils. The free wheel diode reduces the voltage spikes to safe 20-30 volts and redistributes the magnetic energy stored of the coils between the coil and the free wheel diode itself.

For efficient generation of electric field in the treatment area by a PEMF system it is preferred to use pulses with duration about ¼ or less of the time of relaxation of the coil $\tau=L/R$. Here L is the inductance of the coil and R—its resistance. In this case the heat is distributed about equally between the coil and the diode. For longer than ¼ of the time of relaxation pulses the heat is deposited mainly in the coil and the diode remains relatively cool.

In certain embodiments, the pulse duration is preferred to be significantly longer than ¼ of the time of relaxation and the free wheel diode be placed in the controller. That further simplifies the design and manufacturing of the knee and neck applicators.

Figure 24:
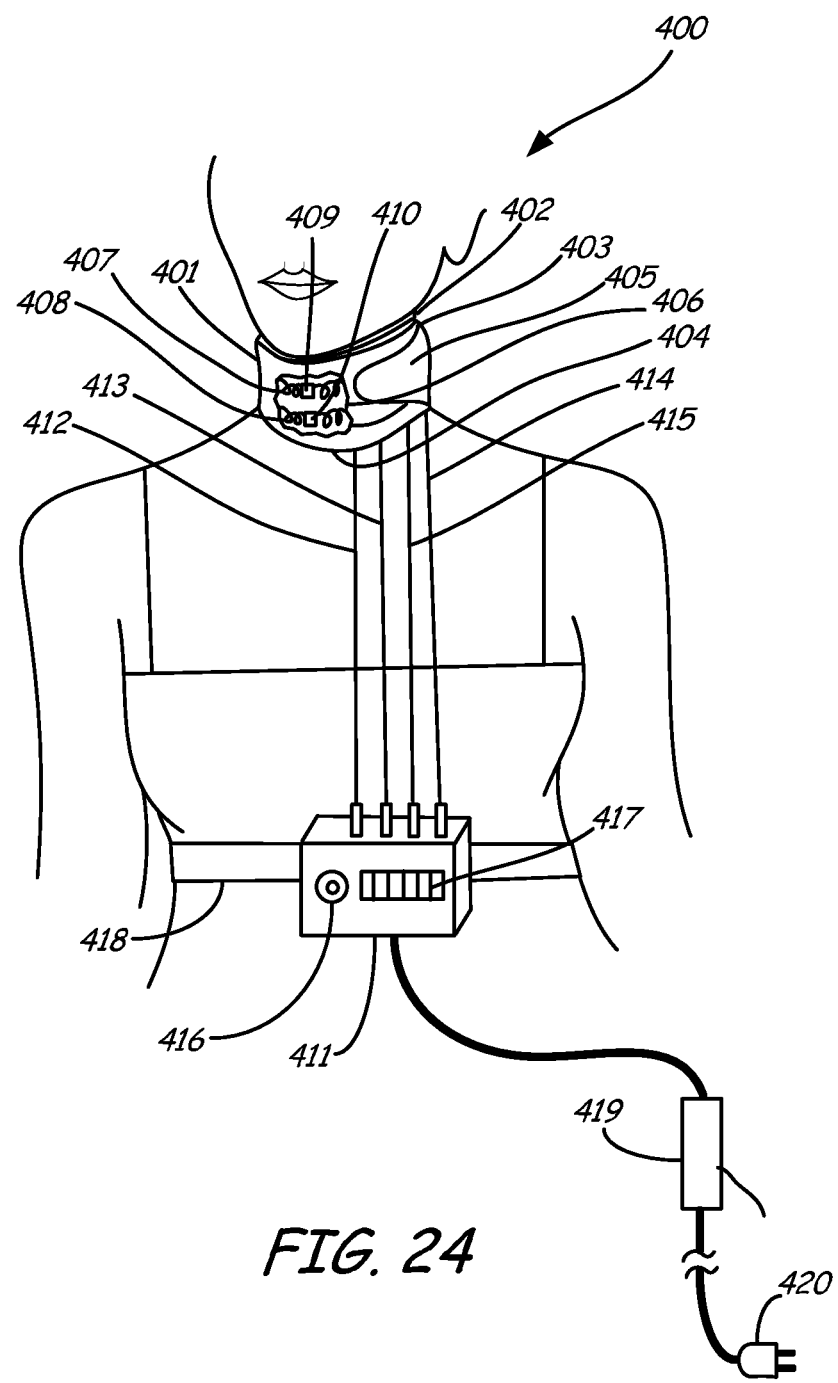
FIG. 24 is an illustration of a neck TA-PEMF applicator according to an example embodiment.

A neck applicator 400 is schematically depicted in FIG. 24. The body of the applicator 401 is positionable around the neck 402. Numeral 403 designates the upper end of the applicator and numeral 404—its lower end. The applicator is secured to the neck 402 by a belt 405 with a Velcro hook-and-loop fastener that is not seen in FIG. 24. It will be described in FIG. 25. The Velcro hook-and-loop fastener comprises two elongated fabric strips which are attached (sewn, adhered, etc) to the opposing surfaces of the applicator 401 and belt 105, one of which includes multiple hooks and the other—loops. (Not shown in the FIG. 24). In a cutoff 406 in the applicator an electromagnetic coil 407 is schematically shown with a thermal sensor 409 secured to it. A thermal sensor 410 is secured to electromagnetic coil 408. The thermal sensors 409 and 410 are designated for monitoring temperatures of coils 407 and 408 and their surroundings. When activated, coils 407 and 408 apply magnetic field in the direction along the neck 402.

Coils 407 and 408 comprise high current solid or multistranded wires with the conductor diameter between 1 and 2 mm. They are connected in parallel to an output of controller 411 via two high current wires 412 and 413.

Thermal sensors 409 and 410 communicate with controller 411 via double wires 414 and 415. Controller 411 includes a control knob 416 which turns on and off the PEMF system and allows selecting a treatment temperature of the applicator by the user. Light diode indicator 417 shows the elected temperature of the treatment. Controller 411 may be secured to a waist belt 418. Controller 411 is powered by a DC power supply 419 connected to an outlet of the power grid by a connector 420, or other suitable power source.

Figure 25:
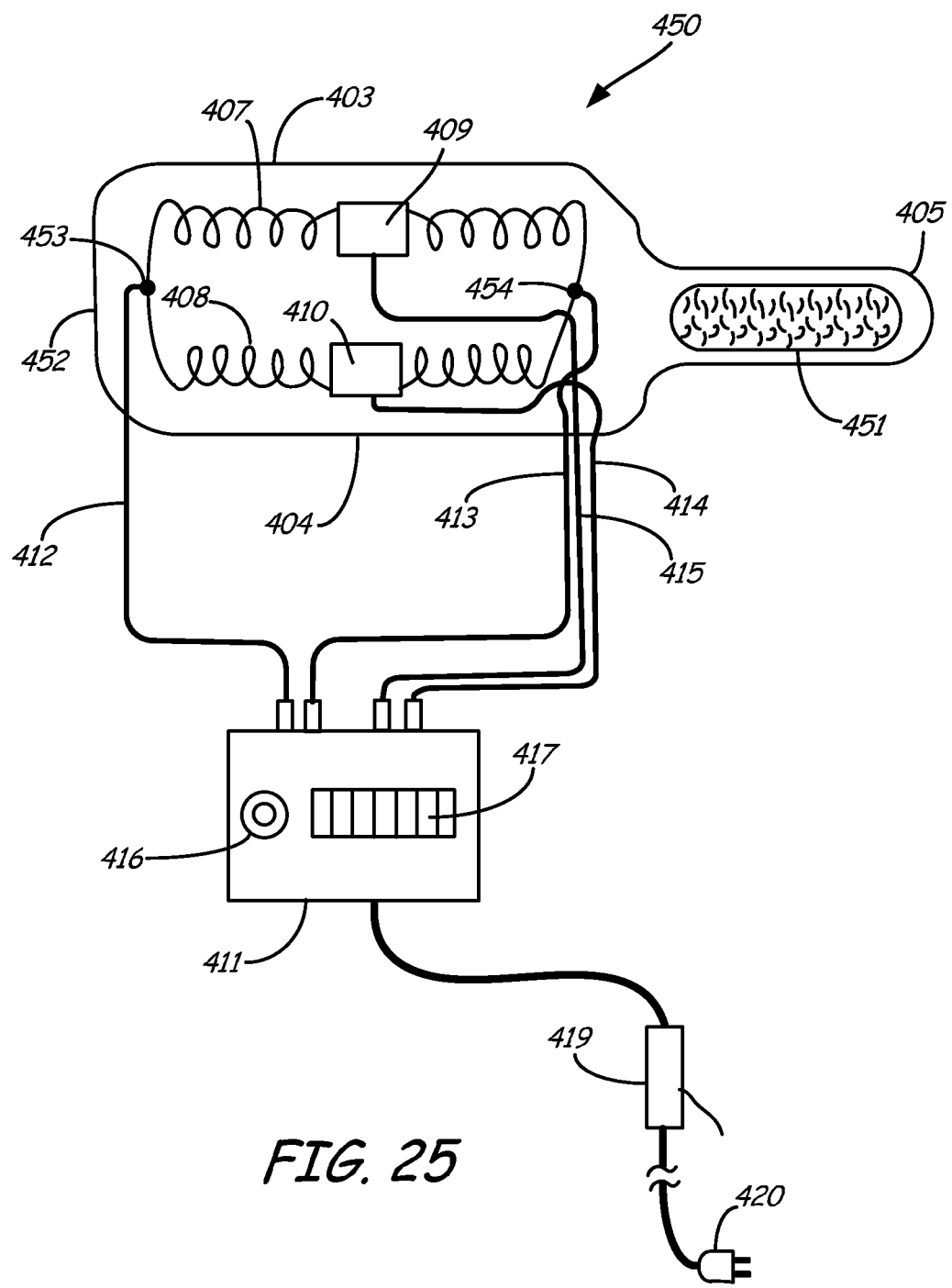
FIG. 25 is another illustration of a neck TA-PEMF applicator according to an example embodiment.

FIG. 25 schematically depicts the neck applicator 450 in unwrapped state. All numerals in FIG. 25 that correspond to the parts visible in FIG. 24 are identical. New numerals in FIG. 25 are described below. Coil 407 and coil 408 are connected in parallel at their ends 453 and 454 by high current wires 412 and 413. Numeral 451 designates a Velcro strip secured on the belt 405. The matching Velcro strip that engages the strip 451 in a wrapped state of the neck applicator is attached to the external side of the neck applicator near its wide end 452 it is not seen in FIG. 25.

Various embodiments of the coils 407 and 408 are shown in FIG. 23. The same way as with the knee applicator, when coils 407 and 408 are wrapped circumferentially around neck 402 they create a magnetic field along and inside the neck that is substantially equivalent to the magnetic field of a simple one turn coil wound around the neck. As was stated above, such a one turn coil would have a very low inductance (small fraction of a microHenry), which makes it very difficult to achieve electromagnetic pulses in duration in the range of tens of microseconds, as preferred by the PEMF system. Both coils 407 and 408 are made of wires several times (three to five) longer than that of a simple one turn coil around the neck and have significantly higher inductance, in the range of 5 to 10 microHenry, which is sufficient for preferred duration of pulses in the PEMF system (20 to 50 microseconds).

The coils shown in FIG. 23 also have significantly larger surface area than that of a one turn coil and provide better conduction of ohmic heat generated in the coils to the treatment area of the neck.

For convenient placement of the neck applicator it does not need disconnection of its wire 412 or 413, it can be easy placed over the head by the user.

Figure 26A:
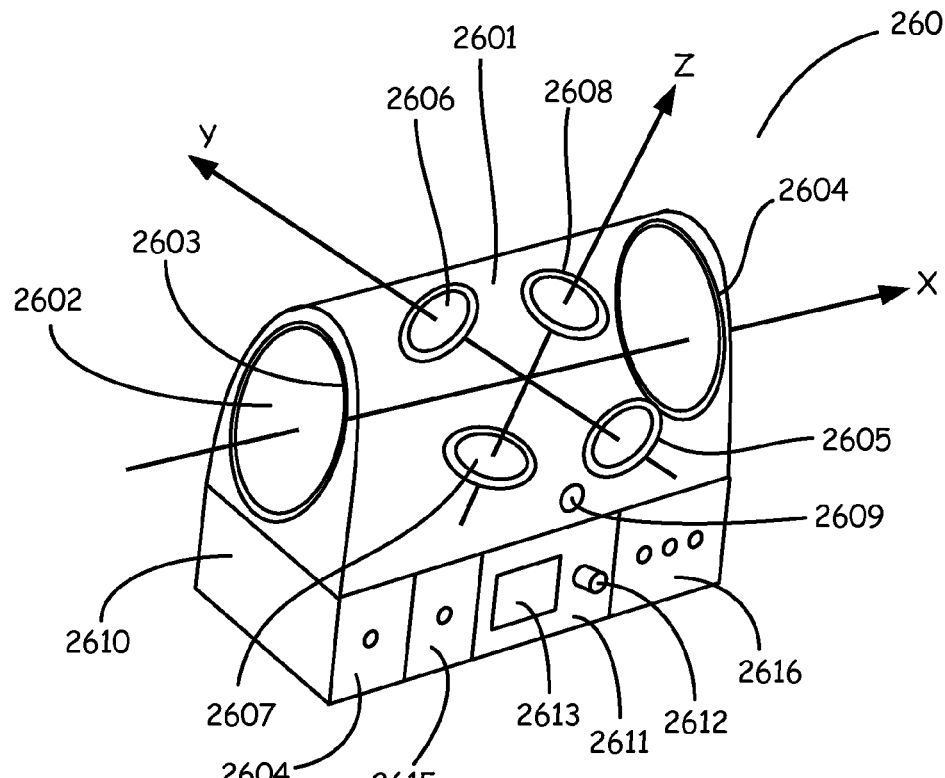
FIG. 26A is an illustration of a hand TA-PEMF applicator according to an example embodiment.

The invention can be configured for application to various different parts of the human body. For example, the hand is one part of the human body that is very often affected by arthritis. One example embodiment of a system employing TA-PEMF for treatment of arthritis of the hand, including the wrist, fingers and the thumb, is shown in FIG. 26A. The system 260 comprises a hollow applicator 2601 having an opening 2602 therethrough and a plurality of electromagnetic coils 2603, 2604, 2605, 2606, 2607, 2608, secured inside of applicator 2601.

A system of coordinates XYZ, with the axis X positioned along the axis of the applicator 2601 and axes Y and Z positioned about 90 degrees to it and to each other, is shown in the FIG. 26A. Coils 2603 and 2604 are arranged around opening 2602 at its opposite ends and are designated to generate magnetic field along the positive direction of the axis X. Coils 2605 and 2606 are placed inside the applicator 2601 to generate magnetic field along the axis Y; coils 2607 and 2608 generate magnetic field along the axis Z. In this embodiment pairs of coils are designated to generate magnetic field along each axis X, Y and Z. Each pair of coils belonging to one axis can by connected to each other parallel or in series. A temperature sensor 2609 is secured on the inside surface of the applicator 2602.

An electronics block or housing 2610 of the TA-PEMF system is disposed on the bottom of the hollow applicator 2601. The block 2610 comprises a computerized controller 2611 with monitoring screen 2613 and user controlled temperature knob 2612, high frequency (HF) generator 2614 utilized for deep heating of the hands inside the applicator 2601, PEMF generator 2615 employed for electromagnetic stimulation and a rechargeable lithium battery 2616.

Figure 26B:
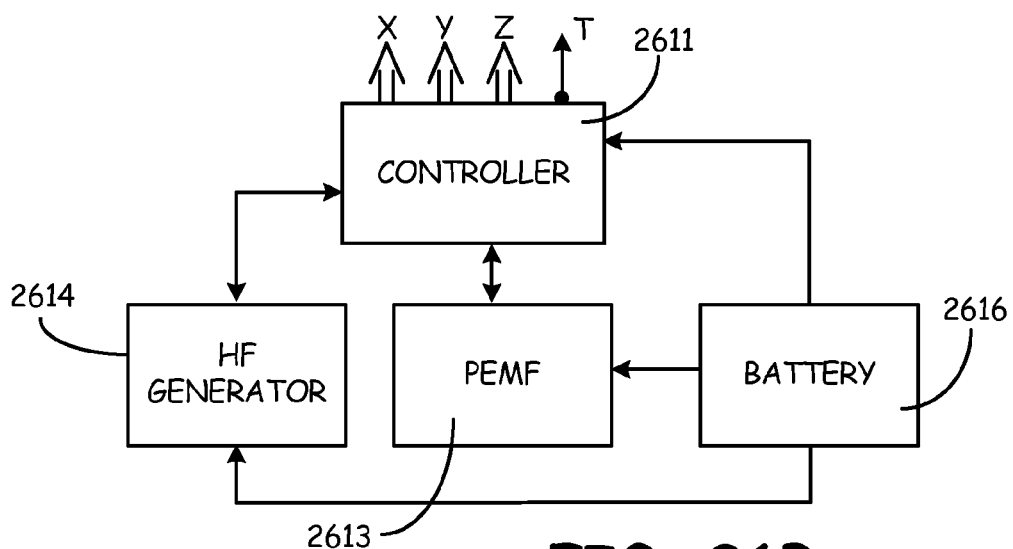
FIG. 26B is a block diagram of a TA-PEMF application system according to an example embodiment.

The functional connections between the different parts of the TA-PEMF system of FIG. 26A are shown in the diagram of FIG. 26B. Computerized controller 2611 is the central part of the system. It controls the power and duration of the heat stimulation signal provided by HF generator 2614 and sequential applications of the HF signal to XYZ coils. It also controls parameters of PEMF stimulation and distribution of the PEMF signal among XYZ coils. During operation of the system the controller 2611 controls alternation between the deep heating and PEMF stimulations. At the beginning of a treatment session, controller 2611 conducts a self-check of the whole system and starts treatment only if the system itself and all its parts operate correctly. It monitors the signal from temperature sensor 2609 and stabilizes the operating temperature by changing parameters of the heat stimulation signal from HF generator 2614. It also defines the duration of treatment.

Multiple joints of the hand and wrist have very complicated 3-dimensional shapes. As discussed earlier herein, the optimal direction of application of pulsed magnetic field for treatment of arthritis is normal to the articular cartilage. In this case, the field lines of induced electric field don't cross the adjacent bones and produce maximum electric fields in the cartilage layer. In the case of magnetic field parallel to a cartilage layer the lines of electric field induced in the joint are directed normally to the cartilage layer. These field lines cross adjacent bones, and electrical resistivity of which is about 100 times higher than that of cartilage. As a result, in accordance with Ohm's law, practically all of the electric field turns out to be applied to the bone tissue, not to the cartilage.

Because of complexity of geometric shapes of joints of the hand and wrist there is no special direction of the magnetic field which would be normal to all articular cartilages at all times. Some segments of the cartilage layers in the treatment zone will be parallel to the magnetic field. In this case almost all electric field will be applied to the bones and no therapeutic effects in cartilage are expected. Magnetic field is a vector and, as any vector, can be presented as a sum of two components: a component normal to the plane of the cartilage layer and parallel to it. As was mentioned earlier, only the normal component induces electric field in the plane of cartilage layer. The other component, parallel to the cartilage, produces electric field mainly in surrounding bones, not cartilages. This component practically does not contribute to the treatment of cartilage. For any direction of applied magnetic field only a component normal to the cartilage layer produces therapeutic effect. This component is equal to the amplitude of the magnetic field multiplied by the cosine of an angle between the vector of magnetic field and a vector normal to the cartilage layer.

One of the novel features of the example embodiment shown in FIG. 26A is its spatial pattern of application of pulsed magnetic fields for treatment of arthritic joints in hand. The pulsed magnetic field is applied to the treatment zone sequentially in 3 different directions. These directions are close to but not necessary orthogonal to each other. These directions are defined by the XYZ set of electromagnetic coils secured to the applicator 2601. With this pattern, every segment of articular cartilage in the treatment zone will be close to normal at least to one of these 3 directions and will get significant value of the induced electric field. If a vector normal to an articular cartilage segment has an angle with applied magnetic field about 45 degrees, the component of the magnetic field that gives full contribution to the induced electric field is about 0.7 times the whole field value. It is thus a sufficient treatment level. Overall, the coverage of the joints with electric field is significantly improved. After a full cycle of three pulses with different spatial distributions the applicator does not leave untreated any part of the cartilages of the wrists, fingers and thumbs.

Another aspect of the invention is that the thermal stimulation of the hand and wrist in this embodiment of TA-PEMF therapy includes deep inductive heating. The inductive coupling of the HF generator 2614 is provided by the same set of XYZ electromagnetic coils which intermittently are connected to PEMF generator 2615 and the HF generator 2614. For the same reason—low electric resistivity of cartilage, the maximum of HF currents from generator 2614 will be induced in the cartilages. A maximum of heat energy will be deposited also in cartilages. This is a significant advantage of the deep inductive heating as compared to the heating with hot pads located outside the treatment zone. The invention allows for much better uniformity of temperatures across the cartilages of the joints.

In one example implementation of the invention, the sequential excitation of XYZ coils by PEMF generator 2614 happens several times per second, exemplary 5 to 10 times, with the time intervals between X, Y and Z pulses about 5-10 milliseconds and the durations of each pulse in the range of about 25-125 microseconds. The electric field created by coils inside the applicator is in the range of 3-20 mV/cm. The power consumed by the PEMF generator and deposited in the applicator during pulsing is about 1-5 W. It does not influence the temperature of the applicator significantly. Between PEMF pulses the coils are disconnected from the PEMF generator 2614 and sequentially connected to the HF generator 2614. The controller 2614 is configured to stabilize the temperature of the applicator by the temperature readings of the sensor 2609 which is in close thermal contact with the applicator. The user can define a comfortable temperature of treatment by changing angular position of the button 2612. The elevated temperature that provides maximum therapeutic effect is about 41-42 degrees C. It can be controlled and maintained by changing parameters of the HF generator by controller 2614. The intensity of deep heating provided by generator 2614 can be modulated by changing its amplitude, duration, or both, by the controller 2611. The power that can be delivered by the HF generator is in the range of 0-50 W. The operating frequency of the HF generator is a constant value in the range of 10-100 MHz. The preferred duration of treatment is 30 minutes. The treatment time is controlled by the controller 2611. However, other treatment durations may be employed.

Figure 27:
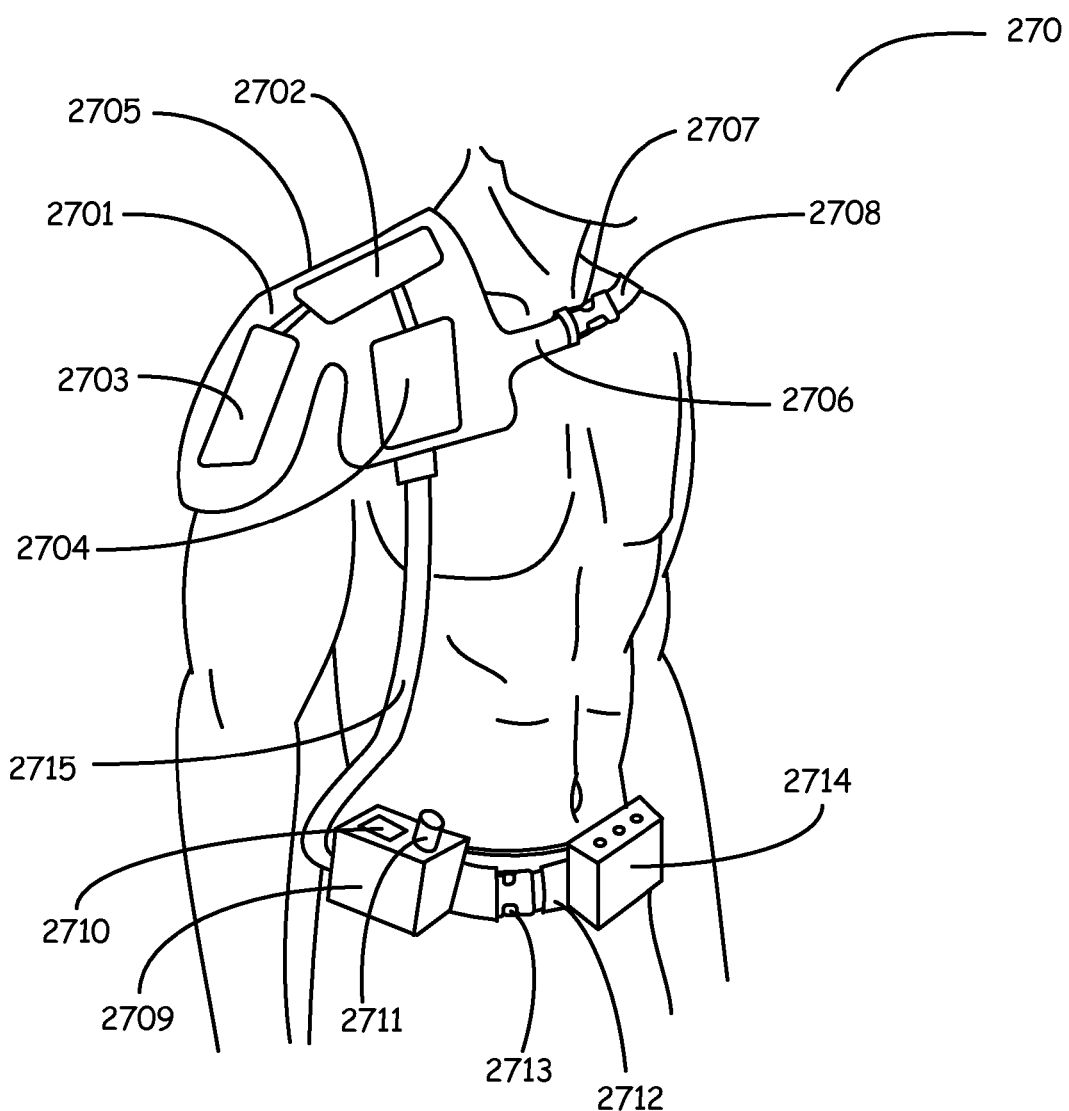
FIG. 27 is an illustration of a shoulder TA-PEMF applicator according to an example embodiment.

A TA-PEMF delivery system 270 for treatment of arthritis of the shoulder according to an example embodiment is schematically shown in FIG. 27. The system 270 comprises a shoulder applicator 2701 having a plurality of electromagnetic coils 2702, 2703, 2704, 2705 secured on the applicator 2701. The coil 2705 is secured on the back side of the shoulder and is not visible in FIG. 27. All coils of the applicator are covered with another layer of fabric not shown in the FIG. 27. A narrow belt 2706 with a buckle 2707 is attached to the applicator 2701. Belt 2708 with a buckle similar to 2707 is attached to the back side of the applicator (not shown).

The applicator 2701 is symmetrical and can be used on both right and left shoulders. The belts 2706 and 2708 enable the user to comfortably secure the applicator 2701 on both shoulders.

Controller 2709 of the TA-PEMF system 270 with monitoring screen 2710 and control button 2711 is secured on the belt 2712 which, in turn, is locked around the waist of the user with buckle 2713. Controller 2709 and the whole system are powered by a rechargeable lithium battery 2714.

All four coils of the applicator 2701 are combined in two pairs: first 2702-2703 and second 2704-2705. The coils in each pair are connected to each other parallel or in series and are energized simultaneously. All coils are imbedded in high thermal conductivity ceramic pads. Each of the pads has a temperature sensor disposed at its center and connected to the controller. Controller 2709 provides DC pulses sequentially to the two pair of coils creating pulsed electromagnetic field in the treatment zone stimulating the shoulder joint. Duration of DC pulses is constant and lays in the range of 10-125 microseconds, repetition rate of the pulsing cycle is variable in the range of 10-250 cycles per second.

The two pair of coils create pulsed magnetic fields in the shoulder joint approximately normal to each other. This field configuration avoids dead zones in the treatment zone. Controller 2709 stabilizes the temperature of the applicator 2701 by changing the repetition rate of between 10 and 250 cycles per second. The user can select a comfortable temperature of the applicator rotating the control button 2711. The electric cable 2715 connecting controller 2709 and applicator 2701 is long enough to be used for both shoulders. The electric field created in the treatment zone is in the range of 3-20 mV/cm. An example preferred treatment regimen is 30 minute, maximum 2 applications a day.

Figure 28:
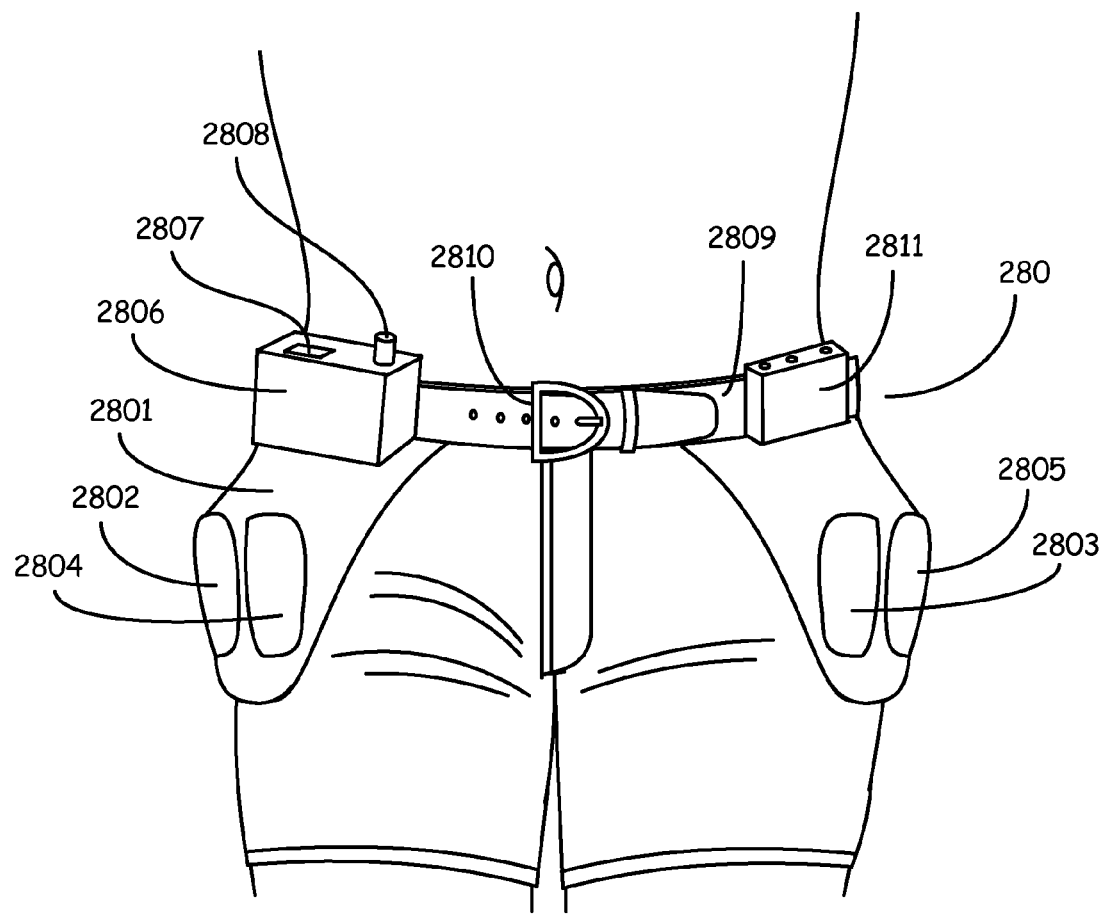
FIG. 28 is an illustration of a hip TA-PEMF applicator according to an example embodiment.

A system 280 employing TA-PEMF for treatment of arthritis of the hips, is schematically shown in FIG. 28. The system 280 comprises hip applicator 2801 having a plurality of electromagnetic coils 2802, 2803, 2804, 2805 secured on the applicator 2801. The coils are imbedded or encapsulated in high thermal conductivity ceramic pads with temperature sensors attached to each of them (not shown in this figure).

The coils are combined in pairs 2802-2803 and 2804-2805, which are connected to each other in parallel or in series and are energized by controller 2806 simultaneously. Controller 2806 with monitoring screen 2807 and control button 2808 are secured to a waist belt 2809 with a buckle 2810. Monitoring screen 2807 is used for displaying information, such as selected temperature level and remaining time of treatment. A rechargeable lithium battery 2811 that powers the system is secured on the belt 2809.

The system 280 is fully controlled by a computerized processor 2806, which defines the sequence and duration of the electromagnetic pulses and the repetition rate of the cycle. Controller 2806 has a small control button 2808 which allows the user to increase or decrease operating temperature of the applicator 2801. Stabilization of the temperature at a user selected level is achieved by changing repetition rate of the cycle of coil pulsing.

During a pulsing cycle each hip joint is stimulated sequentially by one of two adjacent coils at a time. As a result, during a cycle the pulsed magnetic field is applied to a hip joint under different angles, which avoids dead zones in the treatment zone. The parameters of pulses, such as duration, amplitude and repetition rate are similar to other systems disclosed in the application such as system for treatment of spine or shoulder. As in previously described TA-PEMF systems, one preferred treatment regimen is 30 minute, maximum 2 applications a day.

Applicators according to aspects of the invention can be configured to deliver therapy to any arthritic joint in the human body, including for example, foot, ankle, hand, shoulder, elbow, knee, vertebrae and hip joints.

It is also within the scope of the invention to combine features, functions, advantages and aspects of the various embodiments described herein. Thus the embodiments of the invention may comprise combinations of aspects of any one or more of these exemplary embodiments.

While the invention has been described in connection with what is presently considered to be the most practical and preferred example embodiments, it will be apparent to those of ordinary skill in the art that the invention is not to be limited to the disclosed example embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A pulsed electromagnetic field therapy apparatus for delivering treatment to a portion of the spine of a patient, the apparatus comprising:
   an applicator comprising:
      a central portion;
      a first shoulder support extending from the central portion and configured to loop over a first shoulder of the patient;
      a second shoulder support extending from the central portion and configured to loop over a second shoulder of the patient;
      a first belt portion extending from the central portion and configured to wrap in a counterclockwise direction around a waist of the patient; and
      a second belt portion extending from the central portion and configured to wrap in a clockwise direction around the waist of the patient,
      wherein the first shoulder support is securable to the first belt portion on a front side of the patient,
      wherein the second shoulder support is securable to the second belt portion on the front side of the patient, and
      wherein the first belt portion is securable to the second belt portion on the front side of the patient;
   a plurality of electromagnetic coils provided to the central portion of the applicator, the coils configured to generate an electric field and a magnetic field;
   a plurality of free wheel diodes, each of which is disposed in the central portion of the applicator and associated with a respective electromagnetic coil, the plurality of freewheel diodes configured to convert energy of the magnetic field to heat; and
   a control housing disposed on one of the first belt portion and the second belt portion, the housing including a switching board functionally connected to the plurality of electromagnetic coils, a processor functionally connected to the switching board; and a power source electrically connected to the switching board.

2. The apparatus as in claim 1, further comprising:
   a heat source disposed in the central portion of the applicator; and
   a temperature sensor disposed in the central portion of the applicator and functionally connected to the processor to maintain a predetermined treatment temperature.

3. The apparatus of claim 1, wherein the processor is configured to change an operational repetition rate of activation of the plurality of electromagnetic coils by interacting with the switching board.

4. The apparatus of claim 1, wherein the processor is configured to change an electromagnetic pulse duration by interacting with the switching board.

5. The apparatus of claim 1, wherein the processor is configured to provide a repetition rate of activation of the plurality of electromagnetic coils in the range of 10 to 1000 Hertz.

6. The apparatus of claim 1, further comprising a plurality of thermally conductive pads disposed in the central portion of the applicator, each of the pads encapsulating a respective freewheel diode, wherein the heat generated by the freewheel diode is conducted through its respective pad and transmitted to the portion of the patient's spine being treated.

7. The apparatus of claim 1, further comprising a high frequency generator provided to the applicator and electrically coupled to the plurality of electromagnetic coils in the applicator such that high frequency energy from the generator when applied intermittently to the plurality of electromagnetic coils in the applicator generates heat for transmission to the portion of the patient's spine being treated.

8. The apparatus of claim 7, wherein the processor is configured to maintain a predetermined treatment temperature by changing parameters of a signal of the high frequency generator.

9. The apparatus of claim 1, wherein the applicator is configured to orient the plurality of electromagnetic coils in the applicator such that the pulsed magnetic field generated by the plurality of electromagnetic coils is oriented substantially normal to a plane parallel to a vertebral disc of the patient's spine undergoing treatment.

10. A method for treating arthritis in a spinal treatment volume of a human, the method comprising:
    disposing a plurality of thermally conductive pads in a central portion of an applicator located adjacent to a spinal treatment volume, the plurality of thermally conductive pads each including at least one electromagnetic coil;
    looping a first shoulder support over a first shoulder of the patient;
    looping a second shoulder support over a second shoulder of the patient;
    securing the first and the second shoulder supports to the central portion;
    wrapping a first belt portion secured to the central portion in a counterclockwise direction around a waist of the patient;
    wrapping a second belt portion secured to the central portion in a clockwise direction around the waist of the patient;
    securing the first shoulder support to the first belt portion on a front side of the patient;
    securing the second shoulder support to the second belt portion on the front side of the patient;
    securing the first belt portion to the second belt portion on the front side of the patient;
    selectively energizing the electromagnetic coils to generate an electric field and a magnetic field in the spinal treatment volume;
    disposing a free wheel diode in each of the plurality of thermally conductive pads;
    converting the magnetic field's energy into heat via the free wheel diodes;
    conducting the heat from the diodes through the plurality of thermally conductive pads; and
    transmitting the heat to the spinal treatment volume.

11. The method of claim 10, wherein each of the plurality of pads comprises a highly thermally conductive ceramic material, the method further comprising encapsulating the electromagnetic coils and the free wheel diodes in the respective pads.

12. The method of claim 10, further comprising:
    generating a high frequency energy with a high frequency generator electrically connected to the plurality of electromagnetic coils; and
    applying the high frequency energy to the plurality of electromagnetic coils intermittent with the pulsed electromagnetic field with the plurality of electromagnetic coils to generate heat for transmission to the treatment volume.

13. The method of claim 12, further comprising maintain a predetermined treatment temperature by changing parameters of a signal of the high frequency generator.

14. The method of claim 10, further comprising orienting the plurality of thermally conductive pads such that the magnetic field component is oriented substantially normal to a cartilage layer in the treatment volume.

* * * * *